(12) United States Patent
Jonsson et al.

(10) Patent No.: US 9,446,181 B2
(45) Date of Patent: *Sep. 20, 2016

(54) METHOD TO TREAT BLOOD BY CONTROLLING BLOOD PUMPS WITH FLUID PUMPS

(71) Applicant: Gambro Lundia AB, Lund (SE)

(72) Inventors: Lennart Jonsson, Bjarred (SE); Olof Jansson, Vellinge (SE); Mattias Holmer, Lund (SE); Jan Sternby, Lund (SE); Anders Nilsson, Sodra Sandby (SE); Per Hansson, Akarp (SE)

(73) Assignee: Gambro Lundia AB, Lund (SE)

( * ) Notice: Subject to any disclaimer, the term of this patent is extended or adjusted under 35 U.S.C. 154(b) by 386 days.

This patent is subject to a terminal disclaimer.

(21) Appl. No.: 14/075,462

(22) Filed: Nov. 8, 2013

(65) Prior Publication Data

US 2014/0061132 A1 Mar. 6, 2014

Related U.S. Application Data

(62) Division of application No. 12/937,786, filed as application No. PCT/EP2009/054406 on Apr. 14, 2009, now Pat. No. 8,580,110.

(60) Provisional application No. 61/044,960, filed on Apr. 15, 2008.

(30) Foreign Application Priority Data

Apr. 15, 2008 (SE) .................................... 0800861

(51) Int. Cl.
   A61M 1/16 (2006.01)
   A61M 1/10 (2006.01)
   A61M 1/34 (2006.01)

(52) U.S. Cl.
   CPC ............... *A61M 1/16* (2013.01); *A61M 1/106* (2013.01); *A61M 1/1006* (2014.02); *A61M 1/1065* (2014.02); *A61M 1/1601* (2014.02); *A61M 1/34* (2013.01)

(58) Field of Classification Search
   CPC .... A61M 1/16; A61M 1/1006; A61M 1/106; A61M 1/1065; A61M 1/34; A61M 1/1601
   See application file for complete search history.

(56) References Cited

U.S. PATENT DOCUMENTS

| 3,570,672 A | 3/1971 | Bach |
| 3,883,272 A | 5/1975 | Puckett |
| 4,486,189 A | 12/1984 | Troutner et al. |
| 4,552,552 A | 11/1985 | Polaschegg et al. |
| 4,708,802 A | 11/1987 | Rath et al. |
| 4,711,715 A | 12/1987 | Polaschegg |
| 4,828,543 A | 5/1989 | Weiss et al. |
| 5,211,849 A | 5/1993 | Kitaevich et al. |

(Continued)

FOREIGN PATENT DOCUMENTS

| CA | 2474635 | 8/2003 |
| DE | 42 40 681 C2 | 6/1994 |

(Continued)

*Primary Examiner* — John Kim
(74) *Attorney, Agent, or Firm* — Nixon & Vanderhye P.C.

(57) ABSTRACT

A washer press apparatus for washing and dewatering a wide range of solids concentrations of pulp in liquid suspensions includes multiple distinct displacement wash zones about a drum with multiple nips.

15 Claims, 13 Drawing Sheets

(56) References Cited

U.S. PATENT DOCUMENTS

| | | |
|---|---|---|
| 5,910,252 A | 6/1999 | Truitt et al. |
| 6,645,166 B2 | 11/2003 | Scheunert et al. |
| 6,821,441 B2 | 11/2004 | Pedrini et al. |
| 6,899,693 B2 | 5/2005 | Ghelli et al. |
| 7,131,956 B1 | 11/2006 | Pirazzoli et al. |
| 7,780,848 B2 | 8/2010 | Kim et al. |
| 8,485,999 B2 * | 7/2013 | Holmer .................. 210/645 |
| 8,580,110 B2 * | 11/2013 | Jonsson ................ A61M 1/106 210/102 |
| 8,870,804 B2 * | 10/2014 | Jonsson .................. A61M 1/16 604/4.01 |

FOREIGN PATENT DOCUMENTS

| | | |
|---|---|---|
| EP | 0 240 101 A2 | 10/1987 |
| EP | 1 652 541 A1 | 5/2006 |
| WO | 9315825 | 8/1993 |
| WO | 03/070314 A1 | 8/2003 |
| WO | 03066135 | 8/2003 |
| WO | 2005/092408 A1 | 10/2005 |

\* cited by examiner

METHOD TO TREAT BLOOD BY CONTROLLING BLOOD PUMPS WITH FLUID PUMPS

CROSS RELATED APPLICATION

This application is a divisional of and claims priority to U.S. patent application Ser. No. 12/937,786 (now U.S. Pat. No. 8,580,110), filed Oct. 14, 2010 which is a national phase application of PCT/EP2009/054406 filed Apr. 14, 2009, which claims the benefit of Swedish Patent Application No. SE 0800861-7, filed Apr. 15, 2008, and a U.S. Provisional Application No. 61/044,960, filed Apr. 15, 2008, the contents of all of which are incorporated herein by reference.

BACKGROUND OF INVENTION

The present invention relates generally to extracorporeal blood treatment.

A conventional single-needle blood treatment apparatus, for instance a hemodialysis system or a hemodiafiltration system, contains a dialysis fluid circuit and a blood circuit with one or two blood pumps. For patient security reasons, single-needle dialysis is advantageous in a self care setting. Namely, here, there is no risk for dislodgement of a venous needle and thereby loss of blood being pumped out unintentionally via an arterial needle. Additionally, fewer needle punctures to the patient blood access are required relative to dual-needle treatment. Generally, the single-needle system is also well suited for long lasting treatments, such as nocturnal treatments. Moreover, single-needle dialysis may be used when the patient blood access is defective.

The prior art includes a range of examples of solutions for single-needle blood treatment, as well as pump means adapted to such implementations. For example, U.S. Pat. No. 4,552,552 describes a dialysis pumping system for a single-needle dialysis apparatus with a dialyzer having blood and dialysate circuits, and wherein the blood inlets and outlets are joined by intake and outtake lines with at least one blood connection. The intake line has a driving pump and pump valves placed upstream and downstream of the blood pump. The blood pump unit has a generally stiff housing with a diaphragm therein walling off the space in the housing into a first chamber for blood and a second chamber for driving fluid that is joined up with the driving pump. A respective high and low pressure limiting valve means prevent pressure levels outside a given interval by venting the working chamber whenever the pressure falls outside predetermined threshold values.

U.S. Pat. No. 6,645,166 reveals a blood treatment device and disposable kit for a blood treatment device, e.g. a dialysis machine, which permits both single- and dual-needle operation. Here, a blood treatment unit has an inlet connected to a feed line and an outlet connected to a return line. The feed line has two parallel line branches, where a positive displacement pump is connected to a first line branch, and a negative displacement pump is connected to a second line branch. Moreover, a connection line is provided to produce a fluid connection between the outlet of the blood treatment unit and one of the two pumps. For single-needle operation, the feed and return lines are brought together and connected to a common needle.

U.S. Pat. No. 6,899,693 discloses a compact pulsating pumping unit including means suitable to draw blood from an intake connector in order to send it to an outlet connector. Said means are contained in an enclosure provided with valves connected to the inlet and the outlet. An elastic membrane here separates the enclosure into two domes. This allows a working fluid to act on one side of the membrane, such that the membrane acts on blood located on the opposite side. The membrane thereby controls the operation of an inlet valve and an outlet valve, such that blood is moved into respective out from a pumping chamber.

Although the above solutions may have specific beneficial characteristics, they fail to provide an overall optimal fluid flow in a blood treatment apparatus. For example attaining a desired level of ultrafiltration is complicated. Moreover, operating the apparatus requires pressure measurements on the blood side. Hence, the design of the apparatus is compelled to be relatively intricate, and handling the apparatus becomes impractical. This, in turn, renders the apparatus unsuitable for a self care setting. In this respect, the present invention is also advantageous because it requires relatively few interfaces between the apparatus and the disposable units thereof. Furthermore, blood pressure measurements on the blood side are problematic due to the potential risk of infection and contamination of the blood via the pressure measuring means. Specifically, in a self care setting, the patient risks to be stricken with infections caused by his/her own blood residuals from earlier treatments, whereas in a hospital environment infectious substances may be transferred from one patient to another.

SUMMARY OF THE INVENTION

The object of the present invention is therefore to alleviate the above problems and provide an efficient and yet uncomplicated blood treatment solution, which is well adapted for home/self treatment environment.

According to the invention, the object is achieved by the apparatus as initially described, wherein the fluid pumps are configured to control the operation of the blood pumps via the blood treatment fluid. The apparatus is further configured to operate according to a cyclic process of which during a first phase the untreated blood is extracted from the blood source, and during a second phase the treated blood is delivered to the target vessel.

In the apparatus according to the invention the flow of untreated blood extracted from the blood source (access flow) is equivalent to a difference between the second fluid flow of used blood treatment fluid ejected from the apparatus and the first fluid flow of fresh blood treatment fluid drawn from the fluid reservoir.

Likewise, in the apparatus according to the invention the flow of treated blood to the target vessel is equivalent to a difference between the first fluid flow of fresh blood treatment fluid drawn from the fluid reservoir and the second fluid flow of used blood treatment fluid ejected from the apparatus.

Moreover, the apparatus includes a flow control means configured to control a trans-membrane flow between the blood side and the fluid side of the blood treatment unit.

The proposed blood treatment apparatus is advantageous because it renders adjustment of for example the ultrafiltration level a straightforward task.

According to an embodiment of the invention, each of the blood pumps includes a pumping chamber. A flexible member separates the pumping chamber into a first accumulation container and a second accumulation container. The flexible member is movable within the pumping chamber so as to vary a volume relationship between the first and second accumulation containers. The second accumulation container is configured to receive an amount of working fluid to act on the flexible member and thus pump blood to and from the first accumulation container. Moreover, the fluid pumps and the blood pumps are arranged such that the blood treatment fluid constitutes the working fluid for the blood pumps.

According to one embodiment of the invention, the flow control means includes a first flow restrictor that is configured to cause a first pressure drop during operation of the apparatus. The first flow restrictor is arranged in series with the blood treatment unit in a conduit system configured to pass blood through the blood treatment unit. Optionally, the apparatus likewise includes a second flow restrictor. This flow restrictor is arranged in series with the blood treatment unit in a conduit system configured to pass blood treatment fluid through the blood treatment unit.

During operation of the apparatus, the second flow restrictor is configured to cause a second pressure drop. It is further preferable if, during operation of the apparatus, a pressure drop on the blood side of the blood treatment unit and the second flow restrictor is equal to the pressure drop on the fluid side of the blood treatment unit and the first flow restrictor. Thus the respective pressure drop may be set such that an appropriate flow is achieved on the respective side of the blood treatment unit, i.e. such that a trans-membrane flow is attained.

The flow restriction is also configured to provide for synchronized operation of the blood pumps, i.e. the flexible members of the first and second blood pumps reach their respective end positions simultaneously. In operation, when the blood pumps have reached their respective end positions, the fluid pumps may be operated to adjust the trans-membrane flow, i.e. to supply or withdraw fluid from the blood.

According to another embodiment of the invention, the apparatus includes a control unit configured to control the fluid pumps to be operated in such a manner that a base flow is constituted. The base flow is constituted by a flow of blood treatment fluid passing through the blood treatment unit during both the first and second phases of the cyclic process, i.e. the base flow is not passed through the blood pumps. In an alternative embodiment of the invention the base flow in the first phase of the cyclic process is different from the base flow in the second phase of the cyclic process. The base flow is independent of the flow of untreated blood extracted from the blood source. The base flow is also independent of the flow of treated blood delivered to the target vessel. The base flow may be used together with one or more flow control means to control the blood pumps to operate in a synchronized manner by securing the same flow of blood treatment fluid to and from the first and the second accumulation container, respectively. A synchronized operation of the blood pumps ensures that undesired transients in the trans-membrane flow are avoided.

According to still another embodiment of the invention, the base flow may be adjusted during the treatment. A feedback signal received by the control unit includes a blood pressure measurement. The blood pressure measurement is used to control the blood treatment fluid pumps to provide a base flow permitting synchronized operation of the blood pumps. More specifically the feed back signal gives input on when the flexible member in the blood pump reaches its end position by identifying a blood pressure peak. The blood pressure may be measured on a conduit configured to pass fresh blood treatment fluid. Alternatively the blood pressure may be measured by means of a blood pressure meter on a conduit configured to pass blood. The magnitude of the base flow may be chosen such that the flow on the blood treatment fluid side of the blood treatment unit and on the blood side of the blood treatment unit is more or less equal.

In yet another embodiment of the invention the base flow is chosen such that there is a significant difference between the blood treatment fluid flow and the blood flow.

According to yet another embodiment of the invention, the flow control means includes a pair of auxiliary fluid pumps arranged in a conduit system configured to pass blood treatment fluid through the blood treatment unit. Each of the auxiliary fluid pumps is configured to influence a flow of blood treatment fluid that is passed through the blood treatment unit. Specifically, it is preferable if a first auxiliary fluid pump is arranged in an outlet conduit downstream of the blood treatment unit, and the first auxiliary fluid pump is configured to withdraw fluid from the blood being passed through the blood treatment unit. Analogously, a second auxiliary fluid pump is optionally arranged in an inlet conduit upstream of the blood treatment unit. The second auxiliary fluid pump is configured to supply fluid to the blood being passed through the blood treatment unit. Consequently, in operation the pair of auxiliary fluid pumps may be used to control the trans-membrane flow. Since the flow of blood treatment fluid to the blood pumps is controlled by the fluid pumps, synchronized operation of the blood pumps may be provided for without any base flow.

According to a further embodiment of the invention, the flow control means includes first and second adjustable flow restrictors and first and second fluid valve means. The first adjustable flow restrictor is arranged in a first blood-treatment-fluid conduit upstream of the blood treatment unit. The first blood-treatment-fluid conduit is parallel to a conduit in which a first fluid pump of said fluid pumps is arranged. Analogously, the second adjustable flow restrictor is arranged in a second blood-treatment-fluid conduit downstream of the blood treatment unit, and the second blood-treatment-fluid conduit is parallel to a conduit in which the second fluid pump of said fluid pumps is arranged. In this context, parallel means that the second blood-treatment-fluid conduit and the conduit in which the second fluid pump is arranged constitute two branches that originate from a common point. Furtheron, the first fluid valve means is arranged upstream the first adjustable flow restrictor and the first fluid pump in the inlet conduit configured to receive fresh blood treatment fluid into the apparatus. The second fluid valve means is arranged downstream the second adjustable flow restrictor and the second fluid pump in an outlet conduit configured to discharge used blood treatment fluid from the apparatus. By adjusting, during operation, the first and second adjustable flow restrictors and by opening and closing the first and the third fluid valve means alternatingly in the first and second phase respectively of the cyclic process, a desired trans-membrane flow may be attained.

According to a further embodiment of the invention, the flow control means includes four fluid valve means, which are controllable in response to a respective valve control signal, e.g. originating from the control unit. A first fluid valve means is arranged on an inlet conduit configured to receive fresh blood treatment fluid into the apparatus. Downstream of the first fluid valve means the inlet conduit is further connected to the first fluid pump via a first fluid conduit. Downstream of the first fluid valve means the inlet conduit is also further connected to the blood treatment unit via a second fluid conduit means. A third fluid valve means is arranged on the second fluid conduit means between the first fluid valve means and the blood treatment unit. A second fluid valve means is arranged on an outlet conduit configured to discharge used blood treatment fluid from the apparatus. The second fluid valve means is arranged downstream of the blood treatment unit, and is also connected to the second fluid pump. A fourth fluid valve means is arranged on a conduit between the blood treatment unit and the second fluid valve means. By opening and closing, during operation, the first and the third fluid valve means alternatingly in the first and second phase respectively of the cyclic process, and opening and closing the second and fourth fluid valve means intermittently, a desired trans-membrane flow may be attained.

According to another aspect of the invention the object is achieved by the method described initially, wherein the method involves: controlling the blood pumps to operate by passing blood treatment fluid through the fluid pumps, controlling the apparatus according to a cyclic process of which untreated blood is extracted from the blood source during a first phase and treated blood is delivered to the target vessel during a second phase, and controlling a trans-membrane flow between the blood side and the fluid side of the blood treatment unit through the medium of a flow control means. The advantages of this method, as well as the embodiments thereof, are apparent from the discussion above with reference to the proposed apparatus.

According to a further aspect of the invention the object is achieved by a computer program, which is directly loadable into the memory of a computer, and includes software adapted to control the method proposed above when said program is run on a computer.

According to another aspect of the invention the object is achieved by a computer readable medium, having a program recorded thereon, where the program is to control a computer to perform the method proposed above when the program is loaded into the computer.

Clearly, the invention is applicable to dual-needle implementations. However, the proposed solution is especially advantageous for blood treatment in the form of single-needle hemodialysis or hemodiafiltration. The solution is particularly suitable for self care treatment, daily/nocturnal dialysis and intensive care. Further advantages, beneficial features and applications of the present invention will be apparent from the following description and the dependent claims.

BRIEF DESCRIPTION OF THE DRAWINGS

The present invention is now to be explained more closely by means of embodiments, which are disclosed as examples, and with reference to the attached drawings.

DESCRIPTION OF EMBODIMENTS OF THE INVENTION

Figure 1A:
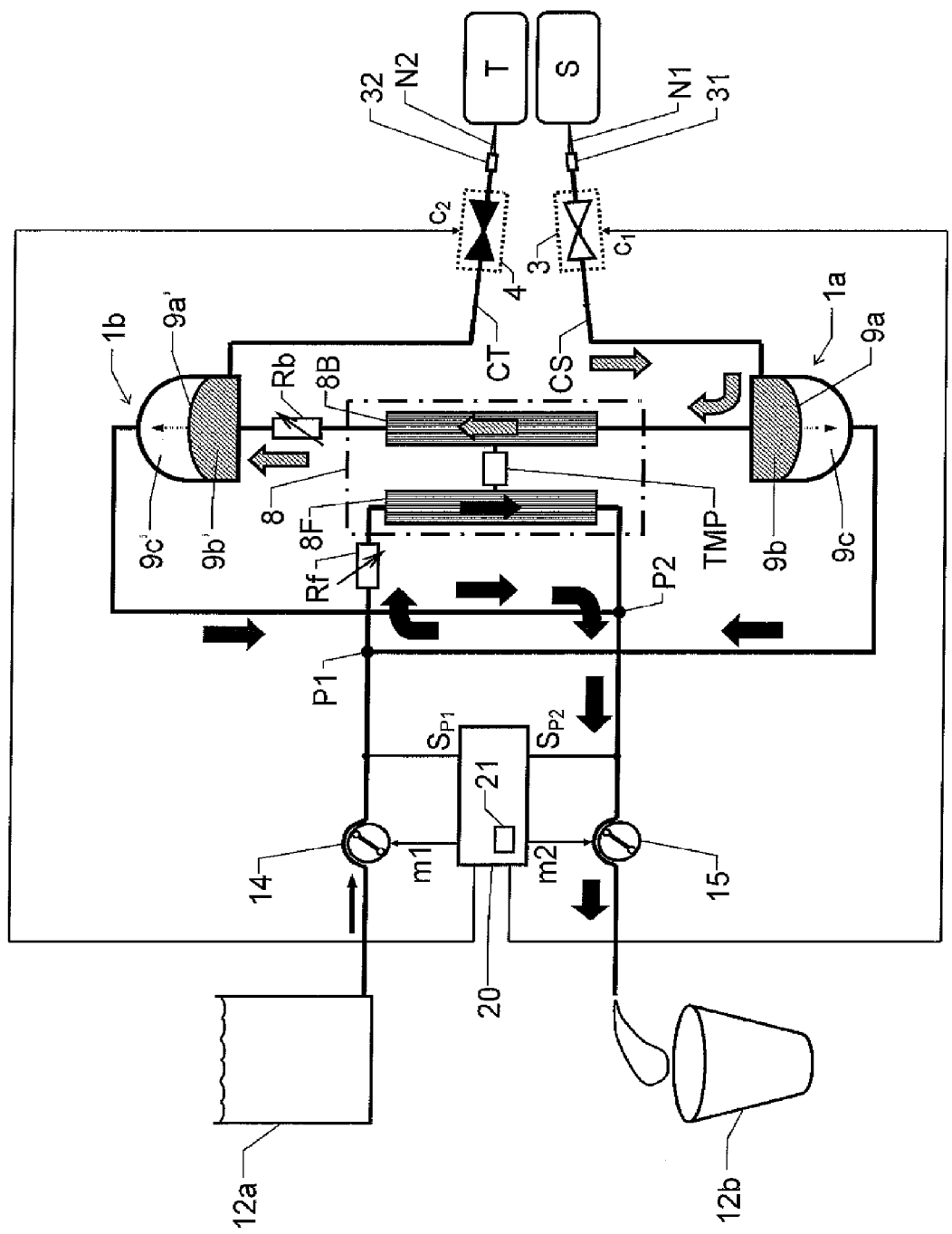
FIGS. 1a-b show block diagrams over a blood treatment apparatus according to a first embodiment of the invention during a first and a second phase respectively of a cyclic treatment process.

We refer initially to FIG. 1a, which shows a block diagram over a blood treatment apparatus (e.g. a dialysis apparatus) according to a first embodiment of the invention during a first phase of a proposed cyclic blood treatment process.

The apparatus includes a blood treatment unit 8 (typically represented by a dialyzer), first and second fluid pumps 14 and 15 respectively and first and second blood pumps 1a and 1b respectively. First and second blood valve means 3 and 4 respectively are also included, which are controlled to be open and closed in an alternating fashion, such that the first blood valve means 3 is open when the second blood valve means 4 is closed, and vice versa.

The blood treatment unit 8 has a blood side 8B and a fluid side 8F that are separated by means of a semi-permeable membrane structure. For example, this structure may be represented by a large number of hollow fibers whose walls constitute a respective semi-permeable membrane and which fibers are configured to transport blood. The structure is also configured to allow blood treatment fluid to be passed outside said fibers when blood is transported there through. Naturally, the opposite situation is equally well applicable, i.e. that blood treatment fluid is passed through the fibers and blood is passed outside thereof. In any case, blood treatment (e.g. dialysis) takes place over each fiber's semi-permeable membrane. Hence, the blood treatment unit 8 is configured to receive untreated blood and fresh blood treatment fluid, and emit treated blood and used blood treatment fluid.

The fluid pumps 14 and 15 are configured to pass blood treatment fluid through the blood treatment unit 8. The blood pumps 1a and 1b are configured to extract untreated blood from a blood source S (e.g. a bag containing blood to be treated, or a patient), pass extracted blood through the blood treatment unit 8 and deliver treated blood to a target vessel T (e.g. a bag for cleaned blood, or a patient). Specifically, the apparatus is controlled to operate according to a cyclic process of which during a first phase untreated blood is extracted from the blood source S, and during a second phase treated blood is delivered to the target vessel T. According to the invention, the fluid pumps 14 and 15 are also configured to control the operation of the blood pumps 1a and 1b via the blood treatment fluid. The apparatus has a flow control means configured to control a trans-membrane flow between the blood side 8B and the fluid side 8F of the blood treatment unit 8. In the first embodiment of the invention illustrated in FIGS. 1a and 1b, a first flow restrictor Rb represents one component of the flow control means.

The first flow restrictor Rb is arranged downstream of a treated-blood outlet from the blood treatment unit 8 and upstream of the second blood pump 1b, which in turn, is configured to deliver the treated blood to the target vessel T. During operation of the blood treatment apparatus, the fluid side 8F is associated with a fluid pressure drop and the blood side 8B is associated with a blood pressure drop. During operation of the apparatus, the first flow restrictor Rb is configured to cause a first pressure drop over the first flow restrictor Rb. As will be explained below, this is advantageous with respect to the proposed control of the trans-membrane flow between blood side 8B and the fluid side 8F.

In an alternative embodiment of the invention a second flow restrictor Rf is arranged upstream of the fluid side of the blood treatment unit 8F. A further alternative embodiment of the invention comprises a first as well as a second flow restrictor Rb, Rf. The second flow restrictor will be described further below.

According to one embodiment of the invention, each of the blood pumps 1a and 1b includes a pumping chamber. A flexible member 9a and 9a' (e.g. in the form of a soft/elastic membrane) separates this pumping chamber into a first accumulation container 9b and 9b' respectively, and a second accumulation container 9c and 9c' respectively. The flexible member 9a and 9a' is movable within its pumping chamber so as to vary a volume relationship between the first and second accumulation containers 9b, 9b' and 9c, 9c' respectively. Furthermore, each second accumulation container 9c and 9c' is configured to receive an amount of working fluid to act on the flexible member 9a and 9a' respectively, and thus pump blood through the first accumulation container 9b and 9b' respectively. According to the invention, the fluid pumps 14 and 15 respectively and the blood pump 1a and 1b are arranged relative to one another, such that the blood treatment fluid constitutes the working fluid for the blood pumps 1a and 1b. Hence, the fluid pumps 14 and 15 control the operation of the blood pumps 1a and 1b via the blood treatment fluid.

During a first phase of the cyclic blood treatment process (FIG. 1a), the second fluid pump 15 is configured to extract/suck fresh blood treatment fluid from the second accumulation container 9c of the first blood pump 1a and draw this blood treatment fluid through the fluid side 8F of the blood treatment unit 8. The operation of the second fluid pump 15 also causes used blood treatment fluid to be extracted/sucked from the second accumulation container 9c' of the second blood pump 1b. After passing the second fluid pump 15, this blood treatment fluid is discharged from the apparatus, e.g. into the drain or a waste compartment 12b.

Figure 1B:
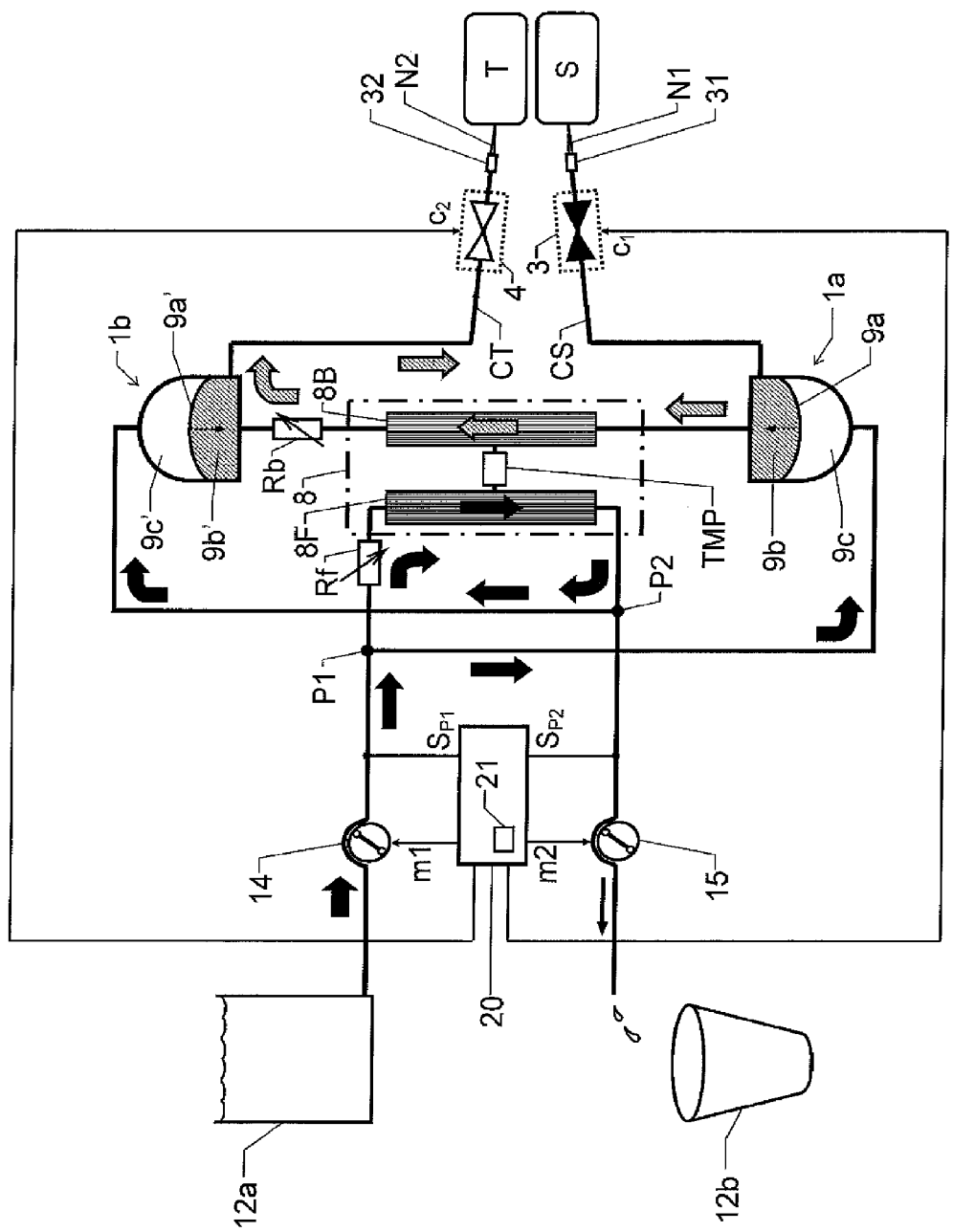

The first fluid pump 14 is configured to draw blood treatment fluid (e.g. dialysis fluid) from a fluid source, such as a reservoir compartment 12a in a second phase of the cyclic blood treatment process (FIG. 1b). Optionally, during the first phase of the cyclic blood treatment process illustrated in FIG. 1a, the first fluid pump 14 draws a relatively small flow of blood treatment fluid (also referred to as base flow which will be further described below), and pumps this fluid directly to a drain or waste compartment 12b via a fluid side 8F of the blood treatment unit 8 (and optionally via a second flow restrictor Rf, which will be described below). Here, the operation of the first and second fluid pumps 14 and 15 causes a trans-membrane flow from the fluid side 8F to the blood side 8B of the blood treatment unit 8.

The above-mentioned first blood valve means 3 is configured to control the extraction of untreated blood from the blood source S via a first needle connector 31 and a first needle N1. Analogously, the above-mentioned second blood valve means 4 is configured to control the delivery of treated blood to the target vessel T via a second needle connector 32 and a second needle N2. Of course, in a single-needle implementation the first and second blood valve means 3 and 4 are instead both connected to one needle, which is attached to a patient's blood system.

In any case, during the first (or blood extraction) phase of the cyclic blood treatment process illustrated in FIG. 1a, the first blood valve means 3 is open and the second blood valve means 4 is closed. As a result, when the second fluid pump 15 pulls the fresh blood treatment fluid out from the second accumulation container 9c of the first blood pump 1a, untreated blood is extracted from the blood source and fed into the first accumulation container 9b of the first blood pump 1a. Incoming blood also continues into the blood side 8B of the blood treatment unit 8. Moreover, since the second fluid pump 15 also draws used blood treatment fluid out from the second accumulation container 9c' of the second blood pump 1b, the blood located on the blood side 8B of the blood treatment unit 8 is further pulled into the first accumulation container 9b' of the second blood pump 1b. Hence, blood passes through the blood treatment unit 8, and as a result, this blood is treated by the blood treatment fluid passing through the fluid side 8F of the blood treatment unit 8.

FIG. 1b illustrates the second (or blood delivery) phase of the cyclic blood treatment process. In this phase, the first blood valve means 3 is closed while the second blood valve means 4 is open. The blood valve means 3 and 4 are controlled via a respective control signal $c_1$ and $c_2$ generated by a control unit 20, which will be discussed in more detail below. In any case, in contrast to the first phase, during the second phase the first fluid pump 14 draws a relatively large flow of fresh blood treatment fluid from the reservoir compartment 12a. The thus extracted blood treatment fluid continues into the second accumulation container 9c of the first blood pump 1a. The entry of fresh blood treatment fluid into the second accumulation container 9c of the first blood pump 1a, in turn, causes untreated blood located in the first accumulation container 9b of the first blood pump 1a to be pushed through the blood side 8B of the blood treatment unit 8.

Moreover, the operation of the first fluid pump 14 causes fresh blood treatment fluid to be extracted/sucked from the reservoir compartment 12a. This blood treatment fluid continues directly into the fluid side 8F of the blood treatment unit 8 (possibly via the above-mentioned flow restrictor Rf). After passing the blood treatment unit 8, the blood treatment fluid continues into the second accumulation container 9c' of the second blood pump 1b. This, in turn, causes blood located in the first accumulation container 9b' of the second blood pump 1b to be ejected into the target vessel via the blood valve means 4, the second needle connector 32 and the second needle N2.

Optionally, during the second phase of the cyclic blood treatment process, the second fluid pump 15 is also operated to some extent. This causes a fraction (a base flow) of the used blood treatment fluid to exit directly from the blood treatment unit 8 (i.e. without being temporarily stored in any of the blood pumps 1a, 1b). The operation of the first and second fluid pumps 14 and 15 during the second phase causes a trans-membrane flow from blood side 8B to the fluid side 8F of the blood treatment unit 8. Thus, by controlling first and second fluid pumps 14 and 15 an amount of fluid drawn from the blood passing through the blood treatment unit 8 may be adjusted.

The first and the second fluid pumps 14, 15 may, as mentioned above, be operated in such a manner that a base flow is constituted. The base flow is constituted by a flow of blood treatment fluid passing through the blood treatment unit 8 during both the first and second phases of the cyclic process, i.e. the base flow is not passed through the blood pumps 1a, 1b. The base flow is independent of the flow of untreated blood extracted from the blood source, S. The base flow may be used together with one or more flow control means to control the blood pumps 1a, 1b to operate in a synchronized manner by securing the same flow of blood treatment fluid to and from the first and the second accumulation container 9c, 9c', respectively. Furtheron, the base flow may be used together with one or more flow control means to control the transmembrane flow.

As mentioned above the blood treatment apparatus may comprise a first flow restrictor Rb. The embodiment shown in FIGS. 1a and 1b also comprises a second flow restrictor Rf which is arranged in series with the blood treatment unit 8 in a conduit system configured to pass blood treatment fluid through the blood treatment unit 8. As mentioned above, during operation of the apparatus, the first flow restrictor Rb is configured to cause a first pressure drop and the second flow restrictor Rf is configured to cause a second pressure drop. The pressure drops over the first and second flow restrictors Rb and Rf are desirable because it facilitates creation of an appropriate trans-membrane flow. The pressure drops over the first and second flow restrictors Rb and Rf are also desirable because it facilitates synchronization of the blood pumps 1a and 1b, i.e. that the flexible members 9a and 9a' are allowed to reach their respective end positions simultaneously.

Optionally, first and second motoric signals m1 and m2 from the control unit 20 control the operation of the fluid pumps 14 and 15 respectively.

Moreover, first and second pressure parameters are optionally measured via a first pressure sensor signal $S_{P1}$ registered on a conduit configured to pass fresh blood treatment fluid from the fluid container 12a into the apparatus, and a second pressure sensor signal $S_{P2}$ registered on a conduit configured to discharge used blood treatment fluid from the apparatus. For reasons of simplicity, we here assume that a pressure measuring unit is included in a control unit 20. In any case, the pressure measuring unit does not come into contact with the blood. Instead, the blood pressure is measured via the blood treatment fluid, which due to the contact with the flexible members 9a and 9a' respectively has a pressure level equal to that of the blood. Specifically, the first pressure parameter represents a first pressure level of the untreated blood extracted from the blood source S, and the second pressure parameter represents a second pressure level of the treated blood being delivered to the target vessel T.

It is further advantageous if the control unit 20, in response to the pressure sensor signals $S_{P1}$ and $S_{P2}$ (expressing the first and second pressure parameters), is configured to control the first and second blood valve means 3 and 4, such that the proposed cyclic process is effected. Of course, this control also involves controlling the fluid pumps 14 and 15 via the motoric signals m1 and m2 respectively. Specifically, during the first phase (the blood extraction phase), the control unit 20 is configured to generate a first control signal c1 such that the first blood valve means 3 is opened, a second control signal c2 such that the second blood valve means 4 is closed. The control unit 20 further produces motoric signals m1 and m2 such that the fluid pumps 14 and 15 are operated as desired. Then, during the second phase (the blood delivery phase), the control unit 20 is configured to generate the first control signal c1 such that the first blood valve means 3 is closed, the second control signal c2 such that the second blood valve means 4 is opened, and motoric signals m1 and m2 such that the fluid pumps 14 and 15 are operated as desired. The control unit 20 uses the first and second pressure parameters to determine appropriate transitions between the first and second phases, and thus control the valve means 3, 4 and the fluid pump 14 and 15 as described above. Optionally, the control unit 20, in turn, includes, or is associated with; a memory means 21 storing computer software for controlling the control unit 20 to effect the above-described procedure.

In a start up phase (i.e. prior to initiating the above-mentioned cyclic process) the fluid circuit may be filled (or more precisely filled, such that superfluous fluid rinses the circuit) with fresh blood treatment fluid (e.g. dialysis fluid) from the fluid container 12a. The filling of the fluid causes any air in the dialysis fluid circuit to be pushed into the waste compartment 12b (or drain) where it is vented. Correspondingly, the first needle N1 may be connected to a saline solution (or other appropriate fluid) to fill and rinse, and thus eliminate any gas bubbles in the blood circuit. This process of filling and rinsing the apparatus is normally referred to as priming.

Figure 2:
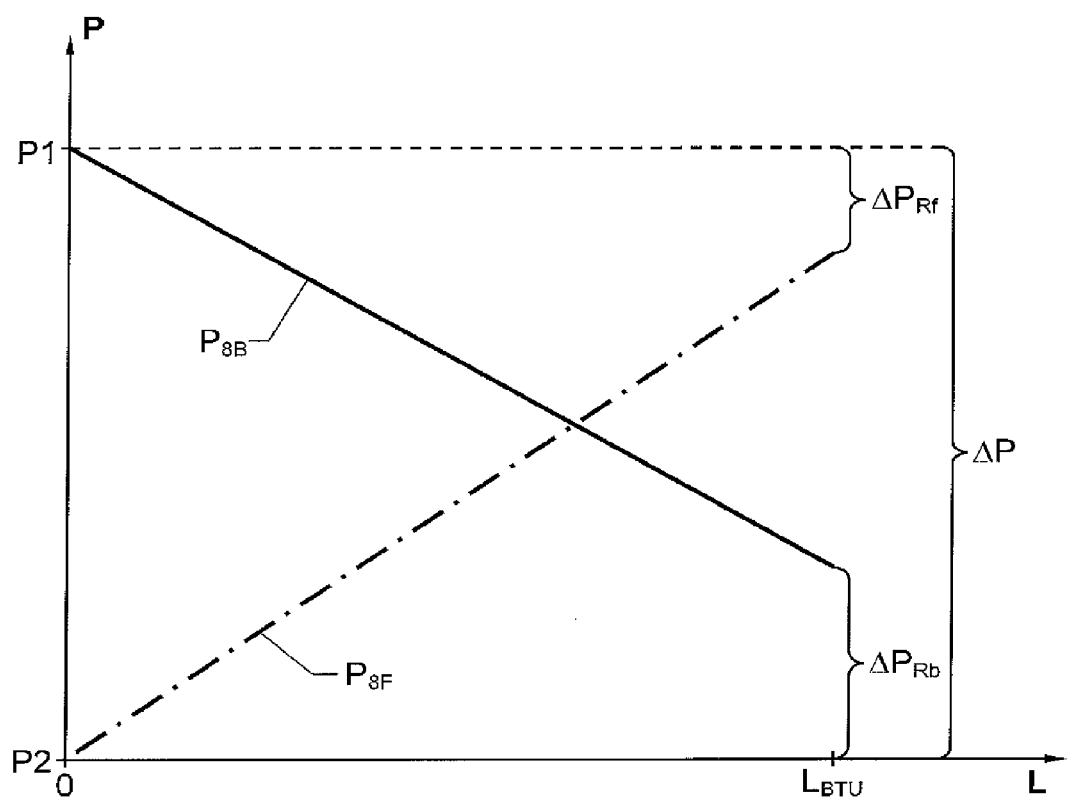
FIG. 2 shows a pair of graphs which elucidate a relationship between a set of pressure drops according to the first embodiment of the invention illustrated in FIGS. 1a and 1b.

FIG. 2 shows an example of a first pressure P8B along the blood treatment unit 8 on the blood side 8B as a function of a length L along the blood treatment unit 8. FIG. 2 also exemplifies of a second pressure P8F along the blood treatment unit 8 on the fluid side 8F as a function of a length L along the blood treatment unit 8. In this example, we assume that the blood treatment unit 8 has length $L=L_{BTU}$. A difference pressure ΔP is defined as the difference between the first and the second pressure points P1 and P2. In FIG. 2, the first pressure drop over the first flow restrictor Rf is designated $\Delta P_{Rf}$ and the second pressure drop over the second flow restrictor Rb is designated $\Delta P_{Rb}$.

A trans-membrane pressure drop TMP between the blood side 8B and the fluid side 8F of the blood treatment unit 8 is given by the expression:

$$TMP = \frac{\Delta P + \Delta P_{Rb}}{2} - \frac{\Delta P - \Delta P_{Rf}}{2} = \frac{\Delta P_{Rb} + \Delta P_{Rf}}{2}$$

In other words, by adequate selection of a combination of blood treatment fluid flows in the first and second phases of the cyclic process and the first and second pressure drops $\Delta P_{Rf}$ and $\Delta P_{Rb}$ respectively (i.e. choosing the characteristics of the first and second flow restrictors Rf and Rb), a desired trans-membrane flow can be attained and thereby ultrafiltration.

Figure 3A:
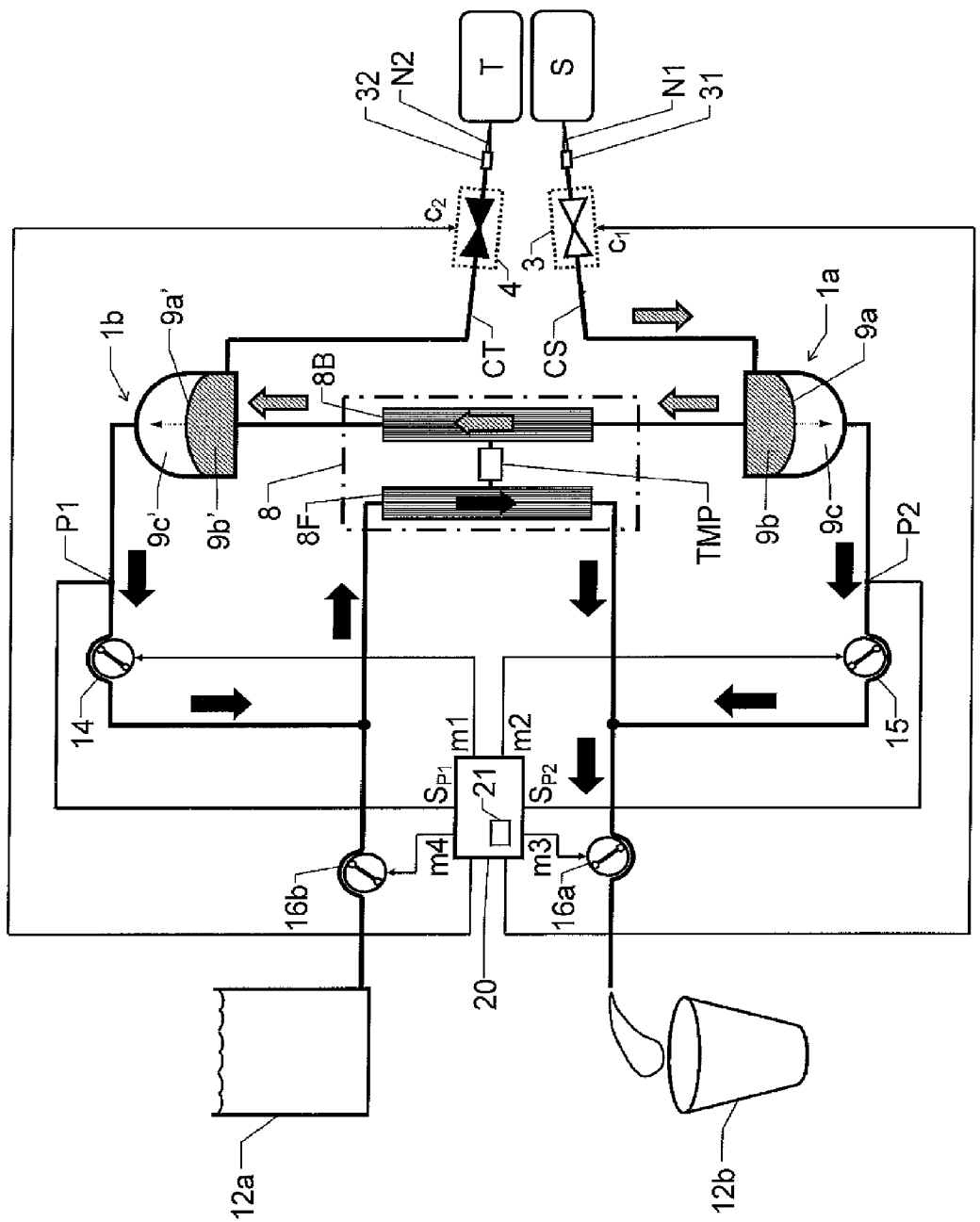
FIGS. 3a-b show block diagrams over a blood treatment apparatus according to a second embodiment of the invention during a first and a second phase respectively of the proposed cyclic treatment process.
Figure 3B:
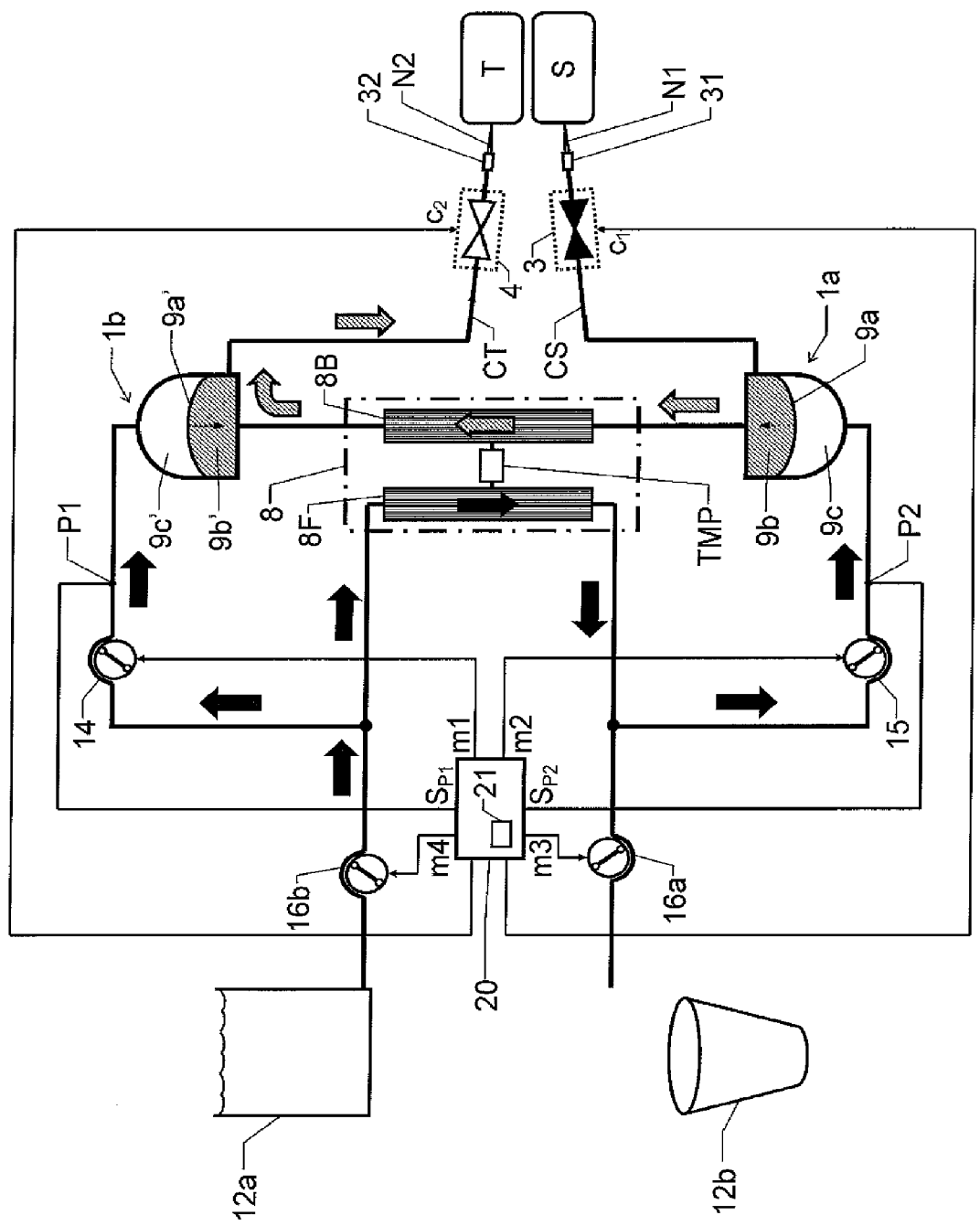

FIGS. 3a and 3b show block diagrams over a blood treatment apparatus according to a second embodiment of the invention during a first and a second phase respectively of the proposed cyclic treatment process. In FIGS. 3a and 3b all units and components having reference signs, which also occur in FIGS. 1a and 1b designate the same units and components as those described above with reference to FIGS. 1a and 1b.

The second embodiment differs from the first embodiment of the invention in that the fluid pumps 14 and 15 are included in the respective fluid paths which connect the blood pumps 1a and 1b to the blood treatment unit 8. In the second embodiment, the first fluid pump 14 is arranged in a conduit between the second blood pump 1b and an inlet configured to receive fresh blood treatment fluid into the blood treatment unit 8. Analogously, the second fluid pump 15 is arranged in a conduit between the first blood pump 1a and an outlet configured to emit used blood treatment fluid from blood treatment unit 8. The first and the second fluid pumps 14, 15 may be controlled to supply and withdraw the same flow to and from the first and the second secondary accumulation containers 9c, 9c'

Furthermore, the flow control means includes first and second auxiliary fluid pumps 16a and 16b instead of the first and second flow restrictors Rb and Rf. In this embodiment of the invention, the first auxiliary fluid pump 16a is located in an outlet conduit downstream of the blood treatment unit 8. The second auxiliary pump 16b is located in an inlet conduit upstream of the blood treatment unit 8. The auxiliary fluid pumps 16a and 16b are configured to influence a flow of blood treatment fluid through the blood treatment unit 8. More specifically the auxiliary fluid pumps 16a, 16b may be adapted to the flows generated by the fluid pumps 14, 15 and thereby control of the trans-membrane flow during the cyclic process. Thus the blood treatment fluid through the blood treatment unit, the blood flow and the transmembrane flow may be adjusted independently. In one embodiment of the invention, during the first phase of the proposed cyclic process, the first auxiliary fluid pump 16a is adapted to control the trans-membrane flow while the second auxiliary pump 16b is idle and, and during the second phase of the proposed cyclic process the second auxiliary fluid pump 16b is adapted to control the trans-membrane flow while the first auxiliary pump 16a is idle. This is illustrated in FIGS. 3a and 3b, where the auxiliary fluid pump 16a is controlled to operate via a motoric signal m3, and the second auxiliary fluid pump 16b is controlled to operate via a motoric signal m4 from the control unit 20. The operation of the auxiliary fluid pumps 16a and 16b causes more or less blood treatment fluid to be ejected into the waste compartment 12b than what is stored in the accumulation containers 9c and 9c' of the first and second blood pumps 1a and 1b respectively. This fluid may originate from the source 12a via the second auxiliary pump 16b, or from the blood side, as a trans-membrane flow, or both. Hence the flow of blood treatment fluid through the blood treatment unit 8 can be more or less than what is controlled by the fluid pumps 14 and 15. The task of auxiliary fluid pumps 16a and 16b is hence to augment the flow through the blood treatment unit 8, as well as to control the trans-membrane flow.

In this embodiment of the invention the first and the second auxiliary pumps 16a, 16b may be operated such that the above described base flow is constituted. However, the base flow is not needed for synchronization of the blood pumps. The magnitude of the base flow is chosen such that the flow on the blood treatment fluid side 8F of the blood treatment unit 8 and on the blood fluid side 8B of the blood treatment unit 8 is more or less equal. Alternatively, the base flow is chosen such that there is a significant difference between the blood treatment fluid flow and the blood flow, e.g. the blood treatment fluid flow is 500 ml/min and the blood flow is 300 ml/min In an alternative embodiment of the blood treatment apparatus shown in FIGS. 3a and 3b the first fluid pump 14 is arranged upstream the second auxiliary pump 16b and the second fluid pump 15 is arranged downstream the first auxiliary pump 16a in order to lessen any transients in the trans-membrane flow. In a further alternative embodiment the first and the second fluid pumps 14, 15 are both arranged upstream the second auxiliary pump 16b or downstream the first auxiliary pump 16a in order to lessen any transients in the trans-membrane flow.

Figure 4A:
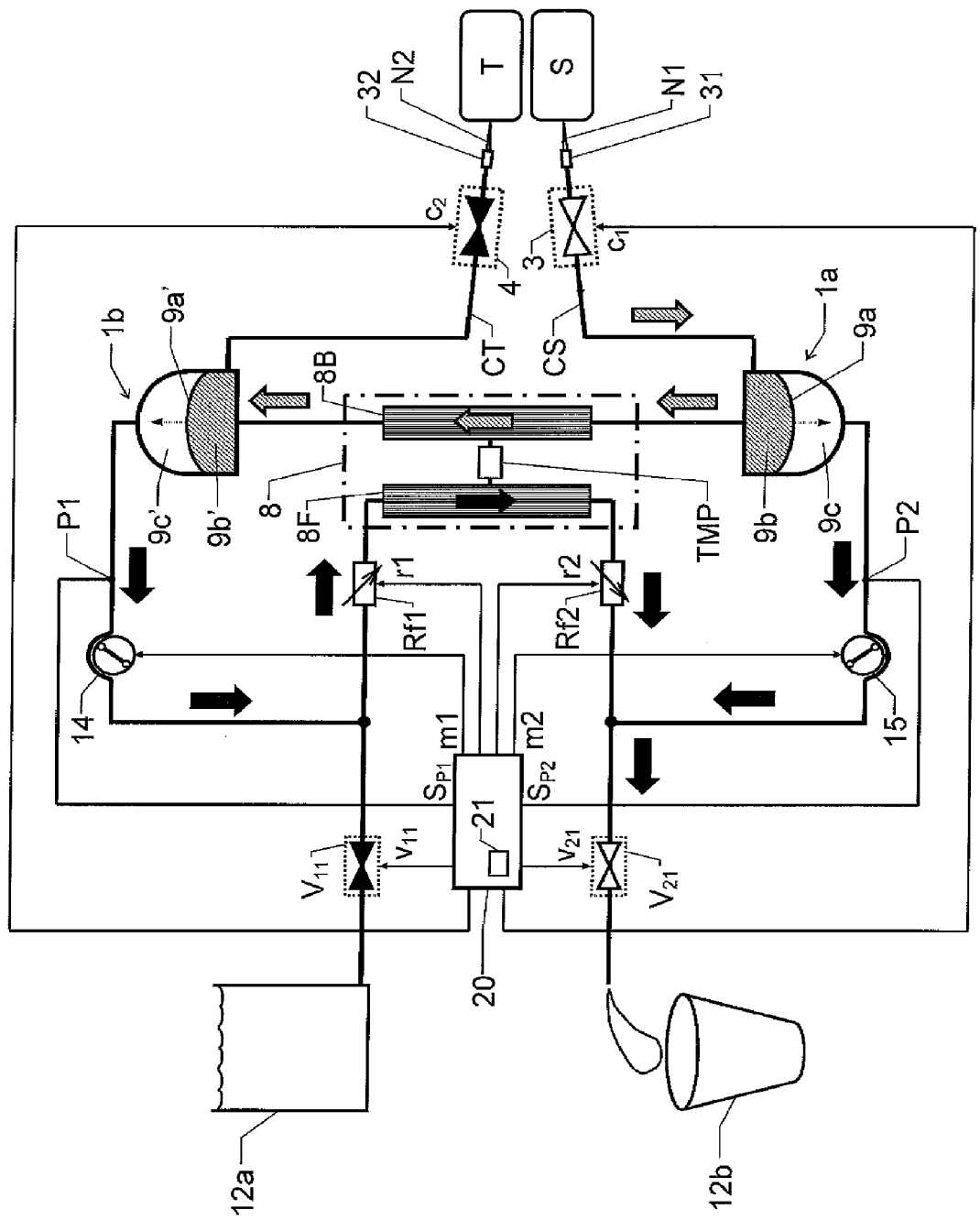
FIGS. 4a-b show block diagrams over a blood treatment apparatus according to a third embodiment of the invention during a first and a second phase respectively of the proposed cyclic treatment process.
Figure 4B:
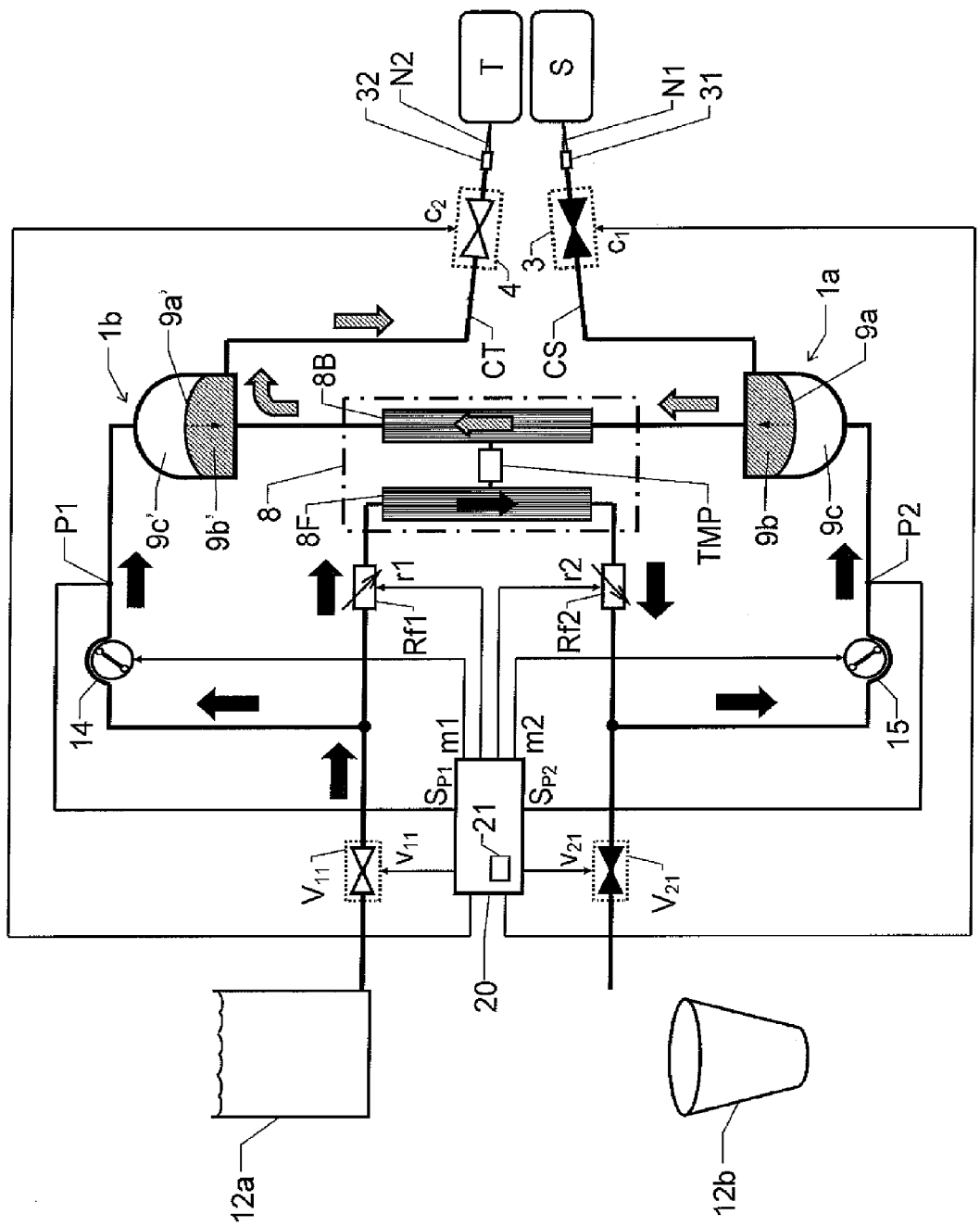

FIGS. 4a and 4b show block diagrams over a blood treatment apparatus according to a third embodiment of the invention during a first and a second phase respectively of the proposed cyclic treatment process. In FIGS. 4a and 4b all units and components having reference signs, which also occur in FIGS. 1a, 1b, 3a and 3b designate the same units and components as those described above with reference to FIGS. 1a, 1b, 3a and 3b.

The third embodiment differs from the second embodiment of the invention in that the flow control means instead of one or more auxiliary fluid pumps, includes first and second adjustable flow restrictors Rf1 and Rf2 respectively. The first adjustable flow restrictor Rf1 is controllable in response to a first restriction control signal r1 from the control unit 20, and the second adjustable flow restrictor Rf2 is controllable in response to a second restriction control signal r2 from the control unit 20

The first adjustable flow restrictor Rf1 is arranged in a first blood-treatment-fluid conduit upstream of the blood treatment unit 8. The first blood-treatment-fluid conduit is parallel to a conduit in which a first fluid pump 14 is arranged. I.e. both the first adjustable flow restrictor Rf1 and the first fluid pump 14 are connected to a conduit configured to receive incoming fresh blood treatment fluid, however the first fluid pump 14 is further connected to the second blood pump 1b whereas the first adjustable flow restrictor Rf1 is further connected to the blood treatment unit 8.

The second adjustable flow restrictor Rf2 is arranged in a second blood-treatment-fluid conduit downstream of the blood treatment unit 8. The second blood-treatment-fluid conduit is parallel to a conduit in which the second fluid pump 15 of said fluid pumps is arranged. In other words, both the second adjustable flow restrictor Rf2 and the second fluid pump 15 are connected to a conduit configured to eject used blood treatment fluid from the apparatus, however the second fluid pump 15 is further connected to the first blood pump 1a whereas the second adjustable flow restrictor Rf2 is further connected to the blood treatment unit 8.

The third embodiment further differs from the second embodiment of the invention in that the flow control means instead of the auxiliary pumps 16a, 16b includes a first and second valve means $V_{11}$ and $V_{21}$, where each valve means is controllable in response to a respective valve control signal $v_{11}$ and $v_{21}$ from the control unit 20.

The first fluid valve means $V_{11}$ is controllable in response to a first valve control signal $v_{11}$. The first fluid valve means $V_{11}$ is arranged on an inlet conduit configured to receive fresh blood treatment fluid into the apparatus. Downstream of the first fluid valve means $V_{11}$ the inlet conduit is further connected to the first fluid pump 14 via a first fluid conduit. Downstream the first fluid valve means $V_{11}$ the inlet conduit is also further connected to the blood treatment unit 8 via a second fluid conduit means and the first adjustable flow restrictor Rf1.

The second fluid valve means $V_{21}$, is controllable in response to a second valve control signal $v_{21}$. The second fluid valve means $V_{21}$ is arranged on an outlet conduit configured to discharge used blood treatment fluid from the apparatus. Specifically, the second fluid valve means $V_{21}$ is arranged downstream of the blood treatment unit 8 via the second adjustable flow restrictor Rf2. Further the second valve means $V_{21}$ is connected to the second fluid pump 15.

By controlling the first and the second valve means $V_{11}$ and $V_{21}$, to alternatingly open and close during the respective first and second phase of the cyclic process and controlling the adjustable flow restrictors Rf1 and Rf2 to appropriate values in the first and second phases of the cyclic process, the transmembrane flow between the blood side 8B and the fluid side 8F of the blood treatment unit 8 may be controlled in a manner equivalent to that described above.

Figure 5A:
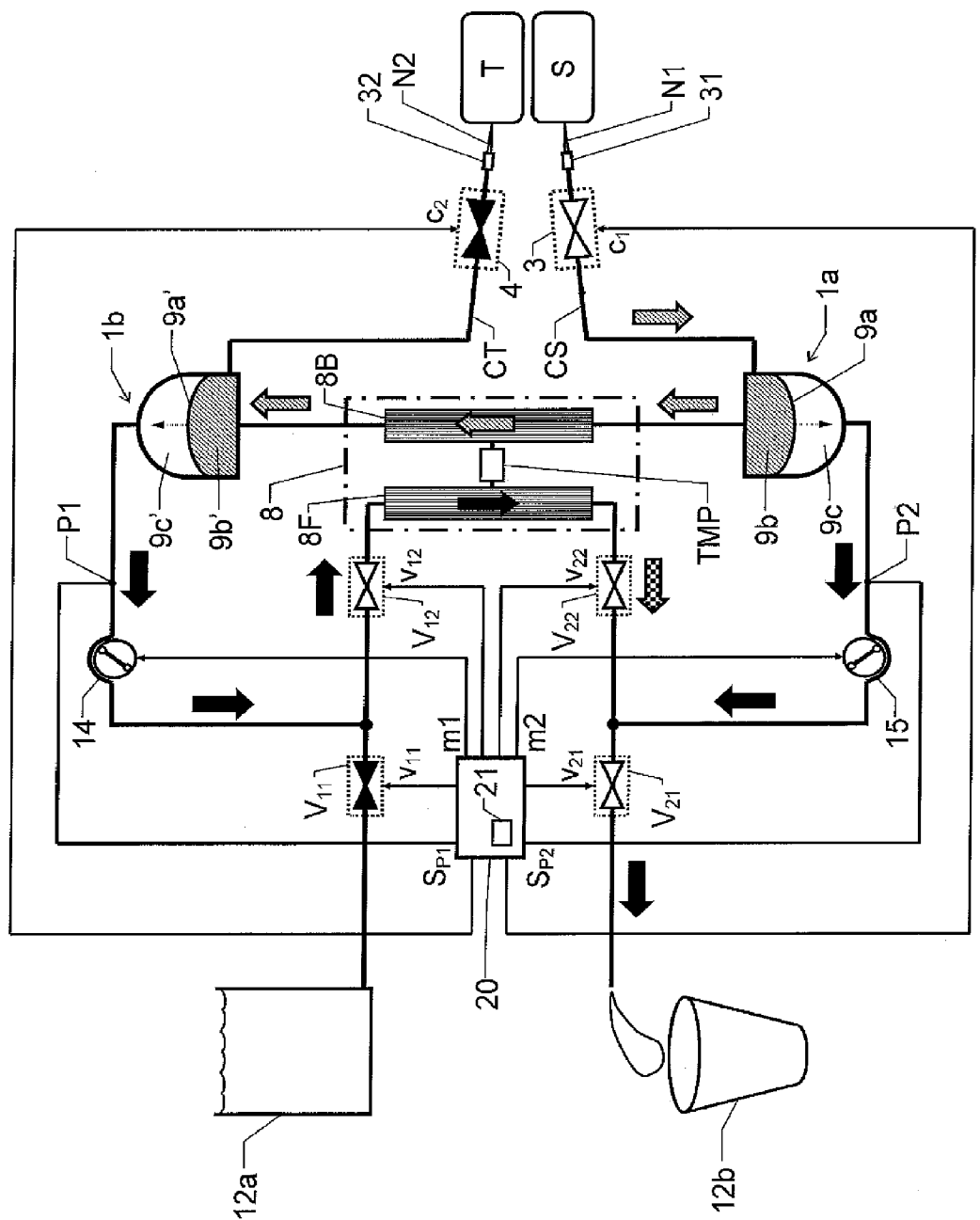
FIGS. 5a-b show block diagrams over a blood treatment apparatus according to a fourth embodiment of the invention during a first and a second phase respectively of the proposed cyclic treatment process.
Figure 5B:
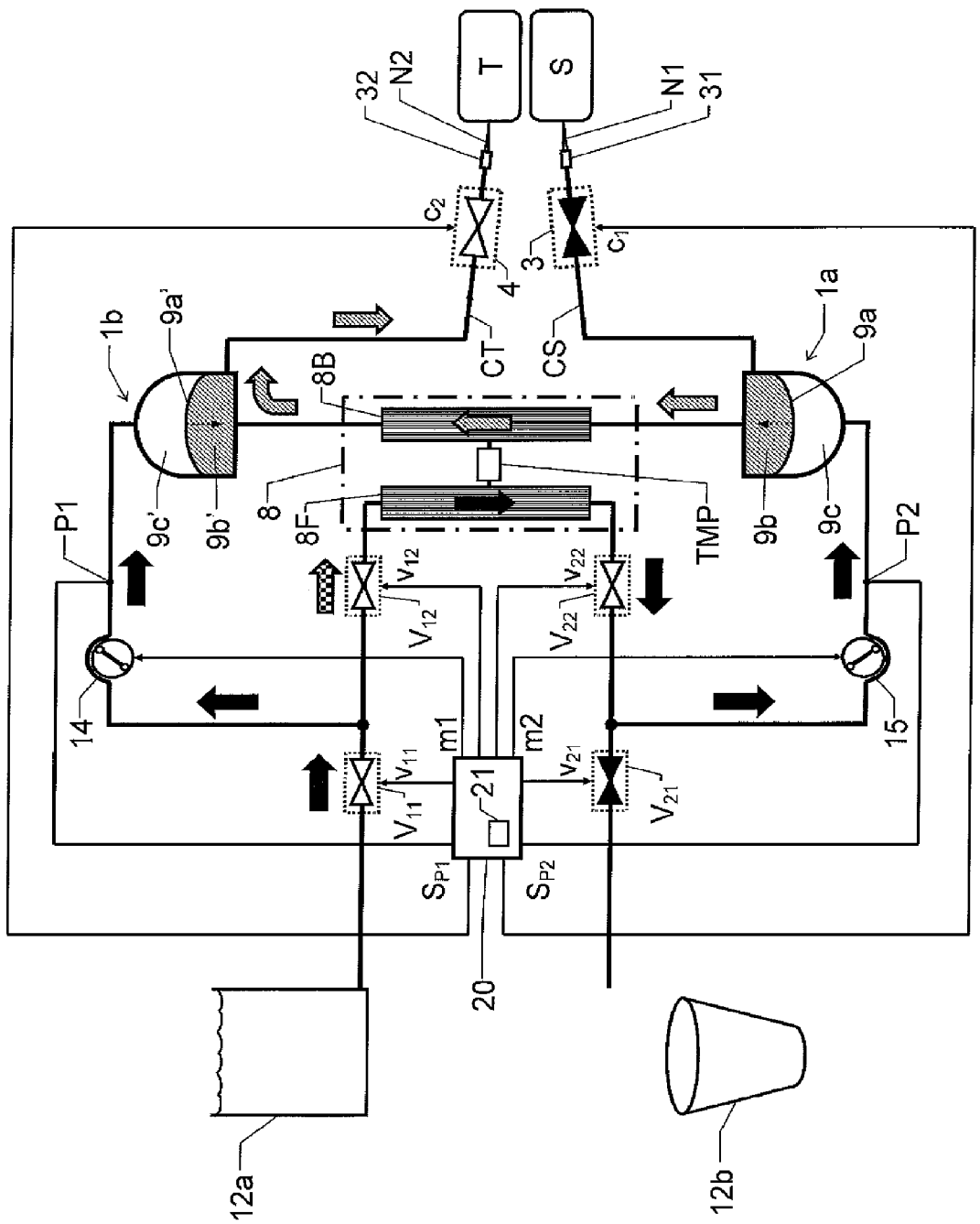

FIGS. 5a and 5b show block diagrams over a blood treatment apparatus according to a fourth embodiment of the invention during a first and a second phase respectively of the proposed cyclic treatment process. In FIGS. 5a and 5b all units and components having reference signs, which also occur in FIGS. 1a, 1b, 3a, 3b, 4a and 4b designate the same units and components as those described above with reference to FIGS. 1a, 1b, 3a, 3b, 4a and 4b.

The fourth embodiment differs from the third embodiment of the invention in that the flow control means, instead of the adjustable flow restrictors, includes a third and a fourth valve means $V_{12}$ and $V_{22}$, where each valve means is controllable in response to a respective valve control signal $v_{12}$ and $v_{22}$ from the control unit 20.

The third fluid valve means $V_{12}$, which is controllable in response to a second valve control signal $v_{12}$, is arranged on the second fluid conduit between the first fluid valve means $V_{11}$ and the blood treatment unit 8.

The fourth fluid valve means $V_{22}$, which is controllable in response to the fourth valve control signal $v_{22}$, is arranged on a conduit between the blood treatment unit 8 and the second fluid valve means $V_{21}$.

Specifically, according to one embodiment of the invention, the control unit 20 is configured to control the fluid valve means $V_{11}$, $V_{12}$, $V_{21}$ and $V_{22}$ as follows. During the first phase (i.e. when blood is being extracted from the blood source S), the control unit 20 controls the first fluid valve means $V_{11}$ to a closed position; the third fluid valve means $V_{12}$ to an open position; and the second valve means $V_{21}$ to an open position. Moreover, the control unit 20 controls the fourth fluid valve means $V_{22}$ in an intermittent manner, between an open and a closed position, such that a desired trans-membrane flow is attained. This is illustrated in FIG. 5a.

FIG. 5b illustrates the second phase (i.e. when blood is being delivered to the target vessel T). During this phase, the control unit 20 controls the first fluid valve means $V_{11}$ to an open position; the third fluid valve means $V_{12}$ in an intermittent manner, between an open and a closed position, such that a desired trans-membrane flow is attained; the second valve means $V_{21}$ to a closed position; and control the fourth fluid valve means $V_{22}$ to an open position.

In order to keep track of the fluid balance between the untreated and the treated blood (e.g. represented by blood extracted from a patient and blood returned to the patient) it is important to measure the trans-membrane flow in each phase of the cyclic process. For example such measurements may be made based on signals registered via first and second flow measurement sensors 33 and 34 respectively (see FIGS. 6a and 6b).

Figure 6A:
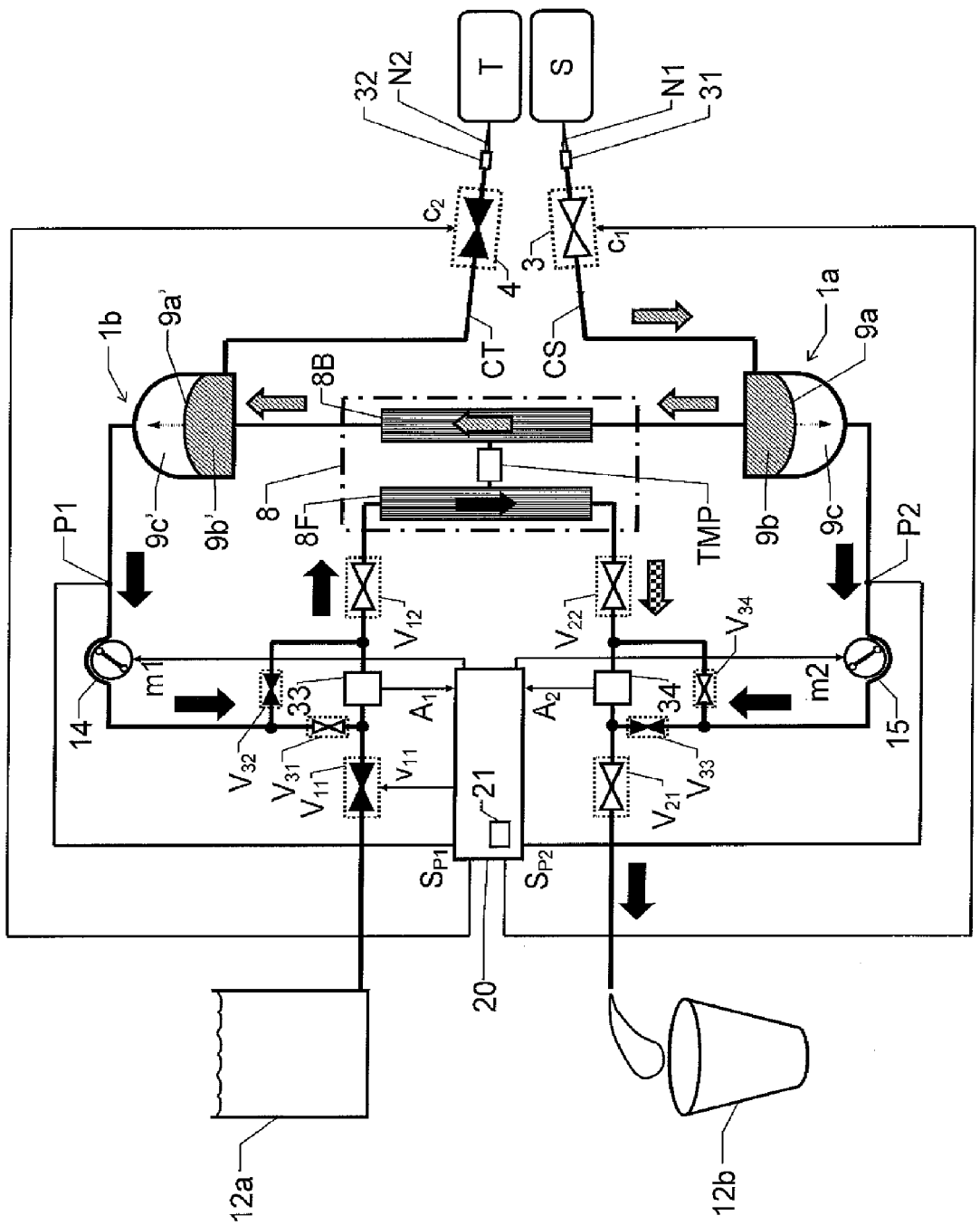
FIGS. 6a-b show block diagrams illustrating the measurement of a trans-membrane flow between the blood side and the a fluid side of the blood treatment unit in the fourth embodiment of the invention.
Figure 6B:
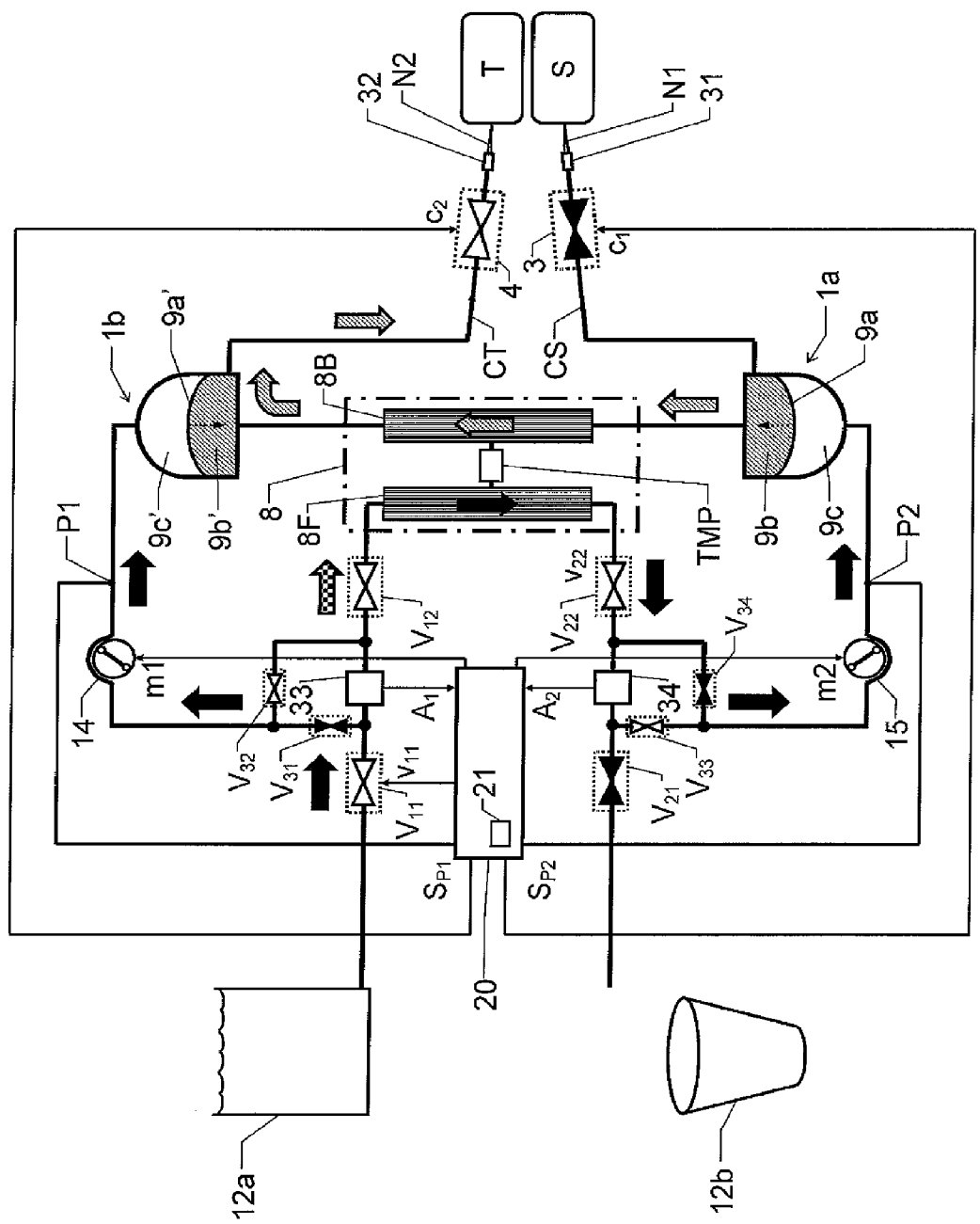

FIGS. 6a and 6b show block diagrams, which illustrate how the trans-membrane flow between the blood side 8B and the a fluid side 8F of the blood treatment unit 8 is measured. In FIGS. 6a and 6b all units and components having reference signs, which also occur in FIGS. 1a, 1b, 3a, 3b, 4a, 4b, 5a and 5b designate the same units and components as those described above with reference to FIGS. 1a, 1b, 3a, 3b, 4a, 4b, 5a and 5b. Here, we have chosen to describe the trans-membrane flow measurement referring to the fourth embodiment of the invention. Nevertheless, the same principle is equally well applicable to any one of the above-described first, second, or third embodiments of the invention, wherein the first measurement sensor 33 is arranged in proximity to the inlet configured to receive fresh blood treatment fluid into the apparatus, and the second flow measurement sensor 34 is arranged in proximity to the outlet configured to eject used blood treatment fluid from the apparatus.

The proposed flow measurement during each phase involves (a) registering a first amount $A_1$ of blood treatment fluid fed into the apparatus, and (b) registering a second amount $A_2$ of fluid ejected from the apparatus. The first flow measurement sensor 33 is configured to deliver the first amount $A_1$ to the control unit 20, and the second flow measurement sensor 34 is configured to deliver the second amount $A_2$ to the control unit 20. Based on these parameters, the control unit 20 is configured to determine an average trans-membrane flow as the difference between the first and second amounts $A_1$ and $A_2$ divided by the duration of the phase in question.

To enable measurement of the first and second amounts $A_1$ and $A_2$ as well as a total amount of blood treatment fluid fed into the apparatus, the third embodiment of the invention shown in FIGS. 6a and 6b includes a set of additional fluid valve means $V_{31}$, $V_{32}$, $V_{33}$, and $V_{34}$. For reasons of clarity, the FIGS. 6a and 6b do not show control lines to these means $V_{31}$, $V_{32}$, $V_{33}$ and $V_{34}$, or to the valve means $V_{12}$, $V_{21}$ or $V_{22}$. However, analogous to the control signal $v_{11}$ in respect of the first fluid valve means $V_{11}$, each of these fluid valve means is controllable via a respective control signal transferred from the control unit 20.

During the first phase illustrated in FIG. 6a (i.e. when blood is being extracted from the blood source S), the control unit 20 is configured to control a first additional fluid valve means $V_{31}$ to an open position; control a second additional fluid valve means $V_{32}$ to a closed position; control a third additional fluid valve means $V_{32}$ to a closed position; and control a fourth additional fluid valve means $V_{34}$ to an open position. The fluid valve means $V_{11}$, $V_{12}$, $V_{21}$ and $V_{22}$ are controlled as described above with reference to FIG. 5a.

During the second phase illustrated in FIG. 6b (i.e. when blood is being delivered to the target vessel T), the control unit 20 is configured to control the first additional fluid valve means $V_{31}$ to a closed position; control the second additional fluid valve means $V_{32}$ to an open position; control the third additional fluid valve means $V_{33}$ to an open position; and control the fourth additional fluid valve means $V_{34}$ to a closed position. The fluid valve means $V_{11}$, $V_{12}$, $V_{21}$ and $V_{22}$ are controlled as described above with reference to FIG. 5b Optionally, the control unit 20 is likewise configured to determine a respective amount of blood treatment fluid fed into the second accumulation container 9c' of the second blood pump 1b during the second phase of the cyclic process and delivered out of the second accumulation container 9c of the first blood pump 1a during the first phase of the cyclic process, as well as a total amount of fluid fed into and taken out of the blood treatment apparatus.

Figure 7:
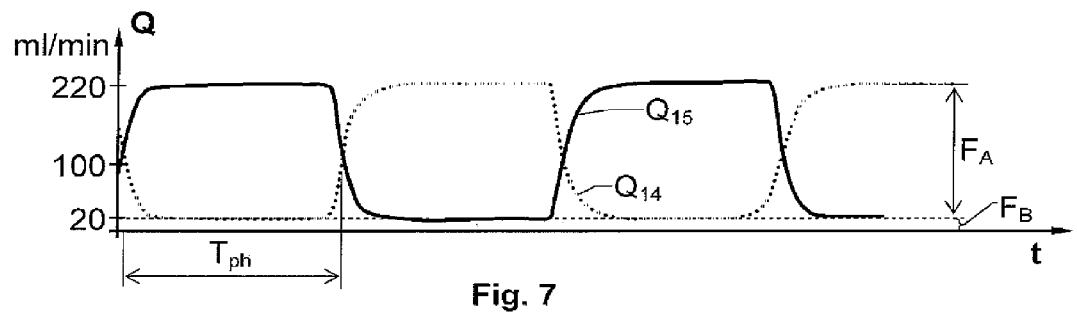
FIG. 7 shows graphs exemplifying how a flow of input fresh blood treatment fluid and a flow of output used blood treatment fluid may vary over time according to one embodiment of the invention.

FIG. 7 shows a first graph $Q_{14}$ exemplifying how a flow of input fresh blood treatment fluid may vary over time t. FIG. 7 also shows a second graph $Q_{15}$ exemplifying how a flow of output used blood treatment fluid may vary over time t. The duration of one phase of the cyclic process is denoted $T_{ph}$ in FIG. 7. Moreover, FIG. 7 illustrates an access flow $F_A$ as a difference between the flow of input fresh blood treatment fluid and the flow of output used blood treatment fluid. The access flow $F_A$ represents a flow of blood extracted from the blood source S. FIG. 7 also shows a base flow level $F_B$ (dashed line), which represents a minimum flow level. As can be seen, in this example base flow level $F_B$ is approximately 20 ml/min.

According to one embodiment of the invention, the control unit 20 is configured to control the first fluid pump 14 to draw fresh blood treatment fluid from the fluid reservoir 12a, control the second fluid pump 15 to eject used blood treatment fluid from the apparatus, such that the access flow $F_A$ attains a desired level.

According to another embodiment of the invention, the control unit 20 is configured to control the fluid pumps 14 and 15 to be operated during the first and second phases of the cyclic blood treatment process in such a manner that the flows $Q_{14}$, $Q_{15}$ of blood treatment fluid passing through the blood treatment unit 8 is equal to or exceeds the base flow level FB during the first phase as well as the second phase of this process. In a further alternative embodiment of the invention the auxiliary pumps 16a, 16b are operated such that the blood treatment fluid passing through the blood treatment unit 8 is equal to or exceeds the base flow level FB during the first phase as well as the second phase of this process.

Figure 8:
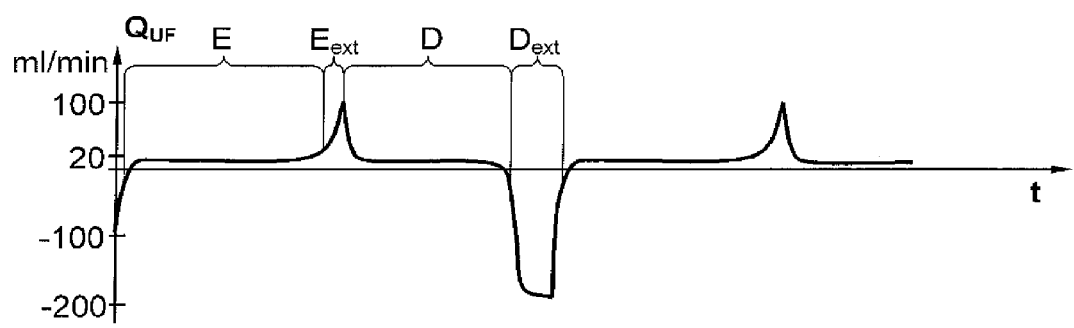
FIG. 8 shows a graph illustrating how a trans-membrane flow between a blood side and a fluid side of the blood treatment unit may vary over time according to one embodiment of the invention.

FIG. 8 shows a graph, which illustrates an example of the trans-membrane flow $Q_{UF}$ between the blood side 8B and the fluid side 8F of the blood treatment unit 8 as a function of time t.

Here, the first phase of the cyclic process includes an extraction period E during which an increasing amount of blood runs into the first accumulation containers 9b and 9b' respectively of the first and second blood pumps 1a and 1b, and an extended extraction period $E_{ext}$ during which the flexible membranes 9a and 9a' are (essentially) positioned in their respective first end positions, and thus no more blood may enter the first accumulation containers 9b and 9b'. As a result, fluid is drawn from the blood during this period $E_{ext}$. Analogously, the second phase of the cyclic process includes a delivery period D during which an increasing amount of blood treatment fluid runs into the second accumulation containers 9c and 9c' respectively of the first and second blood pumps 1a and 1b, and an extended delivery period $D_{ext}$ during which the flexible membranes 9a and 9a' are (essentially) positioned in their respective second end positions, and thus no more blood treatment fluid may enter the second accumulation containers 9c and 9c'. As a result, during this period $D_{ext}$, fluid is transferred to the blood over the semi-permeable membrane. Hence, by adjusting the extended delivery periods $D_{ext}$, an accumulated trans-membrane flow between the blood side 8B and the fluid side 8F of the blood treatment unit 8 can be controlled.

Figure 9:
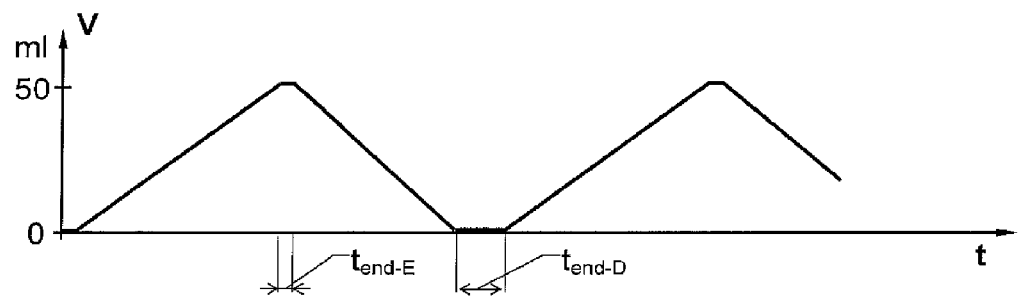
FIG. 9 shows a graph exemplifying a pump-chamber blood volume as a function of time according to one embodiment of the invention.

FIG. 9 shows a graph illustrating the amount of blood stored in one of the blood pumps 1a or 1b as a function of time t corresponding to the trans-membrane flow $Q_{UF}$ of FIG. 8. As is apparent, the first accumulation container 9b or 9b' has a volume of 50 ml, and an interval $t_{end-E}$ during which the chamber 9b or 9b' is completely filled with blood is somewhat shorter than an interval $t_{end-D}$ during which the chamber 9b or 9b' is completely empty (i.e. when the second accumulation container 9c or 9c' is completely filled with blood treatment fluid).

Figure 10:
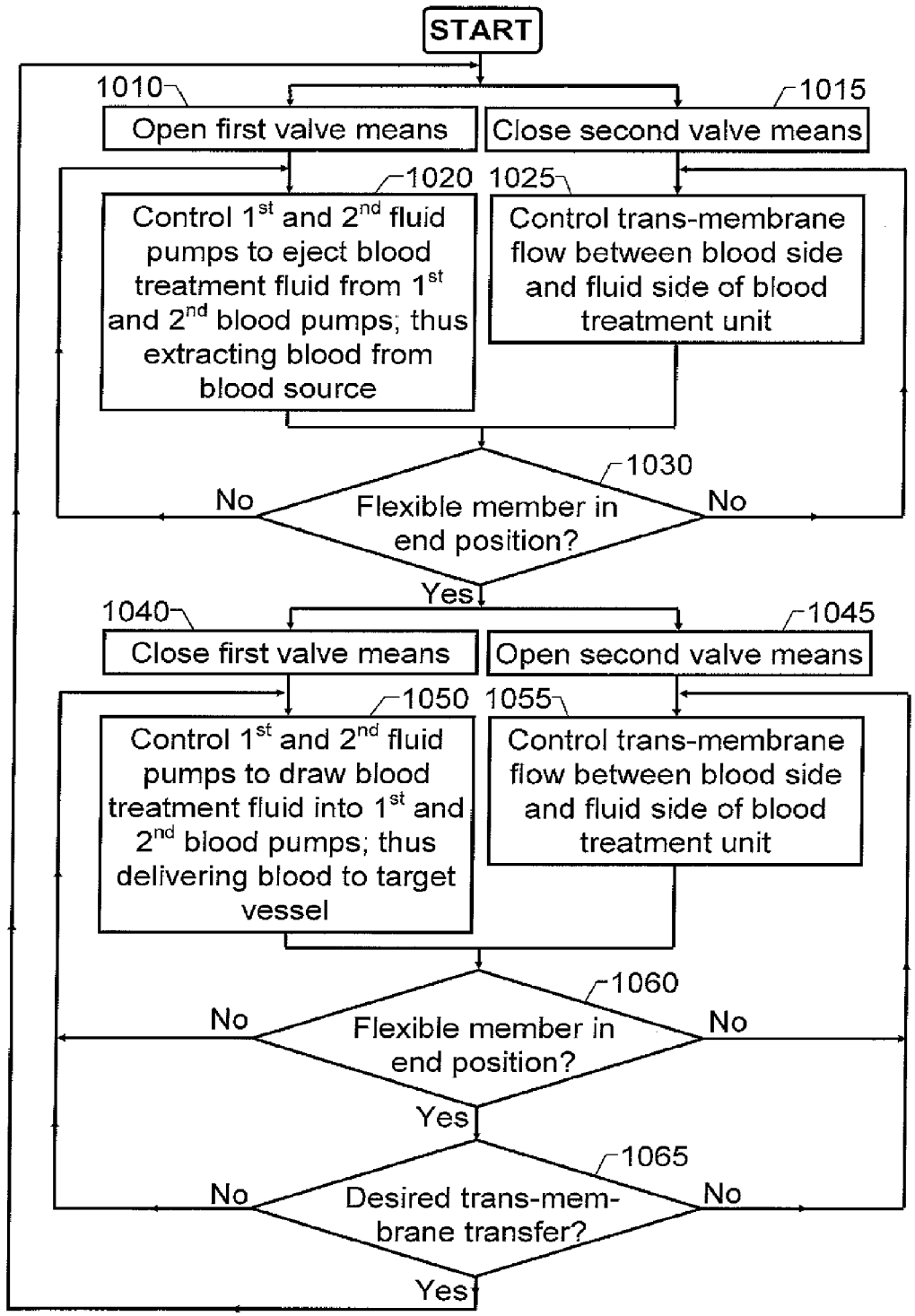
FIG. 10 illustrates, by means of a flow diagram, a general method of operating a blood treatment apparatus according to the invention.

To sum up, we will now describe the proposed method of operating a blood treatment apparatus with reference to the flow diagram of FIG. 10. Here, we presume that the blood treatment apparatus includes: a blood treatment unit configured to receive untreated blood and fresh blood treatment fluid, and emit treated blood and used blood treatment fluid. Moreover, it is assumed that the blood passes on a blood side of a semi-permeable membrane structure and that the blood treatment fluid passes on a fluid side of said structure. A pair of fluid pumps are configured to pass blood treatment fluid through the blood treatment unit and a pair of blood pumps are configured to extract untreated blood from a blood source, pass extracted blood through the blood treatment unit and deliver treated blood to a target vessel.

A first step 1010 opens a first valve means, and in parallel there with a second step 1015 closes a second valve means. Here, the first valve means controls an input of untreated blood from a blood source, and the second valve means controls an output of treated blood to a target vessel.

Thereafter, a step 1020 controls first and second fluid pumps to eject blood treatment fluid, which currently is located in the blood pumps. A first fraction of the blood treatment fluid stored in the second accumulation container of the first blood pump is fresh and passes the blood treatment unit before being ejected from the apparatus, and a second fraction of the blood treatment fluid stored in the second accumulation container of the second blood pump has already passed the blood treatment unit (i.e. is used). As a result of the blood treatment fluid ejection, untreated blood from the blood source is extracted. A first fraction of this blood is stored untreated in the first accumulation container of the first blood pump, and a second fraction of this blood is stored after having passed the blood treatment unit (i.e. as treated) in the first accumulation container of the second blood pump.

In parallel with step 1020, a step 1025 controls a transmembrane fluid flow between the blood side and the a fluid side of the blood treatment unit. This may involve any one of the above-described strategies, for instance exclusively controlling the first and second fluid pumps (cf. the first embodiment of the invention).

Subsequently, a step 1030 checks whether or not the flexible members of the first and second blood pumps have reached their respective end positions. As described above, this conclusion is optionally drawn based on pressure measurements on the fluid side of the apparatus. If in step 1030 it is found that the blood pumps' flexible members have not yet reached their end positions, the procedure loops back to steps 1010 and 1020. Otherwise, case steps 1040 and 1045 follow.

Step 1040 closes the first valve means, and in parallel there with step 1045 opens the second valve means.

Thereafter, a step 1050 controls the first and second fluid pumps to draw blood treatment fluid into the first and second blood pumps. A first fraction of this fluid goes directly to the second accumulation container of the first blood pump, and a second fraction of this fluid passes through the blood treatment unit before entering the second accumulation container of the second blood pump. As a result of the entry of blood treatment fluid, treated blood is delivered to the target vessel. A first fraction of this blood in the first accumulation container of the first blood pump passes the blood treatment unit where it is treated, and a second fraction of this blood located in the first accumulation container of the second blood pump has already passed the blood treatment unit and goes directly to the target vessel.

In parallel with step 1050, a step 1055 controls a transmembrane fluid flow between the blood side and the fluid side of the blood treatment unit. Again, this may involve any one of the above-described strategies.

Then, a step 1060 checks whether or not the flexible members of the first and second blood pumps have reached their respective end positions. If this is found to be the case a step 1065 follows, and otherwise the procedure loops back to steps 1050 and 1055.

Step 1065 checks whether or not a desired trans-membrane fluid transport has been accomplished between the blood side and the fluid side of the blood treatment unit. If this is found to be the case, the procedure loops back to steps 1010 and 1015, and otherwise the procedure loops back to steps 1050 and 1055.

The procedure iterates as described above until the treatment is finalized.

All of the steps, as well as any sub-sequence of steps, described with reference to FIG. 10, above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the procedure according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc), an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant procedures.

In this specification, the wording that: "a fluid pump is arranged in a conduit" shall be understood to also encompass arrangements wherein the pump is configured to operate on a fluid passing through the conduit by other means than having the pump actually included in the conduit, such as hose pumps manipulating the exterior of a fluid conduit.

In this specification is exemplified that the first accumulation container 9b or 9b' has a volume of 50 ml. However, the volume may be smaller or larger, e.g. in the range of 25-75 ml.

The reference to any prior art in this specification is not, and should not be taken as, an acknowledgement or any suggestion that the referenced prior art forms part of the common general knowledge in Australia, or in any other country.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

What is claimed is:

1. A method of treating blood in a blood treatment apparatus including:
a blood treatment unit configured to receive untreated blood and fresh blood treatment fluid, and emit treated blood and used blood treatment fluid, the blood being passed on a blood side of a semi-permeable membrane and the blood treatment fluid being passed on a fluid side of said semi-permeable membrane in the unit; at least one fluid pump configured to pass blood treatment fluid through the blood treatment unit; and at least one blood pump configured to extract untreated blood from a blood source, pass extracted blood through the blood treatment unit and deliver treated blood to a target vessel, the method comprising:
pumping blood by the at least one blood pump while driving the at least one blood pump with blood treatment fluid pumped by the at least one fluid pump,
during a first period, the pumping by the at least one blood pump extracts the untreated blood from the blood source and during a second period the treated blood is pumped by the at least one blood pump into the target vessel, and
controlling a trans-membrane flow between the blood side and the fluid side of the blood treatment unit through the semi-permeable membrane.

2. The method according to claim 1 wherein the controlling of the trans-membrane flow includes at least one of:
restricting a flow of treated blood downstream of the blood treatment unit and upstream of one of said at least one blood pump to create a first pressure drop, and
restricting a flow of the blood treatment fluid in a conduit coupled in series with the blood treatment unit to create a second pressure drop, wherein the first or second pressure drop determines the trans-membrane flow.

3. The method according to claim 1, wherein the controlling of the trans-membrane flow includes controlling a pressure of the blood treatment fluid in a conduit in series with the blood treatment unit wherein the pressure of the blood treatment fluid is controlled by at least one auxiliary fluid pump pumping the blood treatment fluid through the conduit.

4. The method according to claim 1, further comprising: restricting a flow of the blood-treatment fluid through a first conduit segment located upstream of the blood treatment unit and being parallel to a second conduit coupled to a first fluid pump of said at least one fluid pump, and restricting a flow of the blood treatment fluid through a third conduit segment located downstream of the blood treatment unit and being parallel to a fourth conduit coupled to a second fluid pump of said at least one fluid pump.

5. The method according to claim 1, further comprising pumping by the at least one fluid pump the blood treatment fluid at a fluid flow rate through the blood treatment unit during at least one of the first and second periods, wherein the fluid flow rate is at least as great as a base blood flow rate of blood flowing through the blood treatment unit during both the first and second periods.

6. The method according to claim 1 further comprising:
controlling a first fluid pump of said at least one fluid pump to pump the fresh blood treatment fluid from a fluid reservoir at a fresh blood treatment fluid rate,
controlling a second fluid pump of said at least one fluid pump to pump the used blood treatment fluid from the apparatus at a used blood treatment fluid rate,
controlling said at least one fluid pumps to drive the at least one blood pump during the first period to pump the untreated blood from the blood source at a blood flow rate equivalent to a difference between the fresh blood treatment fluid rate and the used blood treatment fluid rate, and controlling said at least one fluid pump to drive the at least one blood pump during the second period to pump treated blood to the target vessel at a blood flow rate equivalent to a difference between the used blood treatment fluid rate and the fresh blood treatment fluid rate.

7. The method of claim 1 wherein the blood source and target vessel are a vascular system of a human patient.

8. A blood treatment apparatus comprising:
a blood treatment unit configured to receive untreated blood and fresh blood treatment fluid, and emit treated blood and used blood treatment fluid, the blood being passed on a blood side of a semi-permeable membrane and the blood treatment fluid being passed on a fluid side of said semi-permeable membrane;
a fluid pump configured to pass blood treatment fluid through the blood treatment unit;
a blood pump configured to extract untreated blood from a blood source, pass extracted blood through the blood treatment unit and deliver treated blood to a target vessel,
a computer including a non-transitory memory storing instructions which are executed by the computer and cause the apparatus to:
drive the blood pump to pump blood wherein the blood pump is driven with blood treatment fluid pumped by the fluid pump, and
during a first period, the pumping by the blood pump extracts the untreated blood from the blood source and during a second period the pumping by the blood pump infuses the treated blood into the target vessel.

9. The blood treatment apparatus of claim 8 wherein the instructions when executed by the computer further cause the apparatus to achieve a certain trans-membrane flow through the semi-permeable membrane during at least one of the first and second periods by controlling the fluid pump.

10. The blood treatment apparatus of claim 8 wherein the blood source and target vessel are a vascular system of a human patient.

11. The blood treatment apparatus of claim 8 wherein the blood pump includes a pair of blood pumps and the fluid pump includes a pair of fluid pumps.

12. A non-transitory computer readable medium for a blood treatment apparatus including a blood treatment unit configured to receive untreated blood and fresh blood treatment fluid, and emit treated blood and used blood treatment fluid, the blood being passed on a blood side of a semi-permeable membrane and the blood treatment fluid being passed on a fluid side of said semi-permeable membrane; a fluid pump configured to pass blood treatment fluid through the blood treatment unit; a blood pump configured to extract untreated blood from a blood source, pass extracted blood through the blood treatment unit and deliver treated blood to a target vessel, and a computer, wherein the non-transitory computer readable medium stores instructions which are configured to be executed by the computer and cause the apparatus to:
drive the fluid pump to pump the blood treatment fluid to the blood pump, wherein the blood pump is driven by the blood treatment fluid to pump blood,
during a first period, drive the blood pump to extract the untreated blood from the blood source and during a second period drive the blood pump to infuse the treated blood into the target vessel, and
control a trans-membrane flow between the blood side and the fluid side of the blood treatment unit through the semi-permeable membrane.

13. The non-transitory computer readable medium of claim 12 wherein the instructions when executed by the computer control the transmembrane flow by controlling the pumping of the blood treatment fluid by the fluid pump.

14. The non-transitory computer readable medium of claim 12 wherein the blood source and target vessel are a vascular system of a human patient.

15. The non-transitory computer readable medium of claim 12 wherein the instruction to drive the blood pump include instructions to drive a pair of blood pumps, and the instructions to drive the fluid pump include instructions to drive a pair of fluid pumps.

* * * * *

UNITED STATES PATENT AND TRADEMARK OFFICE
CERTIFICATE OF CORRECTION

PATENT NO. : 9,446,181 B2  
APPLICATION NO. : 14/075462  
DATED : September 20, 2016  
INVENTOR(S) : Jonsson et al.

Page 1 of 1

It is certified that error appears in the above-identified patent and that said Letters Patent is hereby corrected as shown below:

On the Title Page

At item (57), replace the entire Abstract with:

- A proposed blood treatment apparatus includes: a blood treatment unit (8), a pair of fluid pumps (14, 15) and a pair of blood pumps (1a, 1b). The blood treatment unit (8) is configured to receive untreated blood and fresh blood treatment fluid, and emit treated blood and used blood treatment fluid. The fluid pumps (14, 15) are configured to pass blood treatment fluid through the blood treatment unit (8). The blood pumps (1a, 1b) are configured to extract untreated blood from a blood source (S), pass extracted blood through the blood treatment unit (8) and deliver treated blood to a target vessel (T). Additionally, the fluid pumps (14, 15) are configured to control the operation of the blood pumps (1a, 1b) via the blood treatment fluid. Moreover, a flow control means (16a) is configured to control a trans-membrane flow between the blood side (8B) and the a fluid side (8F) of the blood treatment unit (8). Hence, for instance ultrafiltration can be adjusted to a desired level in a very straightforward manner. -

Signed and Sealed this  
Twenty-fourth Day of January, 2017

Michelle K. Lee  
*Director of the United States Patent and Trademark Office*